United States Patent
Kruth et al.

(10) Patent No.: US 12,257,445 B2
(45) Date of Patent: Mar. 25, 2025

(54) THERAPY DEVICE

(71) Applicant: Piomic Medical AG, Zurich (CH)

(72) Inventors: Jari Henrik Mitja Kruth, Zurich (CH); Marc André Walter, Zurich (CH); Christopher Maximilian Constantin Richard Hertz, Zurich (CH); Juerg Hans Froehlich, Zurich (CH); Martin Walti, Zurich (CH); Florian Eberli, Wil (CH); Sven Zwicker, Wil (CH)

(73) Assignee: Piomic Medical AG, Zurich (CH)

( * ) Notice: Subject to any disclaimer, the term of this patent is extended or adjusted under 35 U.S.C. 154(b) by 981 days.

(21) Appl. No.: 17/295,095

(22) PCT Filed: Nov. 28, 2019

(86) PCT No.: PCT/EP2019/082896
§ 371 (c)(1),
(2) Date: May 19, 2021

(87) PCT Pub. No.: WO2020/126392
PCT Pub. Date: Jun. 25, 2020

(65) Prior Publication Data
US 2022/0096856 A1    Mar. 31, 2022

(30) Foreign Application Priority Data
Dec. 18, 2018  (DE) .................. 10 2018 009 941.6

(51) Int. Cl.
*A61N 2/00* (2006.01)
*A61B 17/00* (2006.01)
(Continued)

(52) U.S. Cl.
CPC .............. *A61N 2/002* (2013.01); *A61N 2/02* (2013.01); *A61N 5/0616* (2013.01);
(Continued)

(58) Field of Classification Search
None
See application file for complete search history.

(56) References Cited

U.S. PATENT DOCUMENTS

| 5,752,911 A | 5/1998 | Canedo et al. |
| 7,744,522 B2 | 6/2010 | Vancraeyenest |

(Continued)

FOREIGN PATENT DOCUMENTS

| AU | 2007201559 | 5/2007 |
| CA | 2981424 | 10/2016 |

(Continued)

OTHER PUBLICATIONS

Maxim Integrated. (Jan. 31, 2001). Reverse-current circuitry protection. Reverse-Current Circuitry Protection | Analog Devices. https://www.analog.com/en/design-notes/reversecurrent-circuitry-protection.html (Year: 2001).*

(Continued)

*Primary Examiner* — Carrie R Dorna
*Assistant Examiner* — Marc D. Honrath
(74) *Attorney, Agent, or Firm* — Williams Mullen; Thomas F. Bergert

(57) ABSTRACT

We describe an optical and magnetic stimulation, OMS, wound therapy device comprising: a light source configured to generate an optical field for an OMS wound therapy; an electric circuit coupled to the light source for driving the light source to generate the optical field; a coil configured to generate a magnetic field for the OMS wound therapy; and a magnetic field shield arranged between the coil on the one hand and the light source and electric circuit on the other hand, and wherein the magnetic field shield is configured to shield the electric circuit and the light source from the magnetic field generated by the coil.

21 Claims, 19 Drawing Sheets

(51) Int. Cl.
*A61B 18/00* (2006.01)
*A61N 2/02* (2006.01)
*A61N 5/06* (2006.01)

(52) U.S. Cl.
CPC .............. *A61B 2017/00057* (2013.01); *A61B 2018/00904* (2013.01); *A61N 2005/0626* (2013.01); *A61N 2005/0645* (2013.01); *A61N 2005/0651* (2013.01); *A61N 2005/0659* (2013.01); *A61N 2005/0663* (2013.01)

(56) References Cited

U.S. PATENT DOCUMENTS

| | | | |
|---|---|---|---|
| 2009/0005631 | A1 | 1/2009 | Simenhaus et al. |
| 2009/0240310 | A1* | 9/2009 | Kennedy .............. A61N 5/0616 607/88 |
| 2012/0143285 | A1* | 6/2012 | Wang .................... G06Q 40/00 607/59 |
| 2012/0296150 | A1* | 11/2012 | Pletnev .................... A61N 2/02 600/13 |
| 2014/0249495 | A1 | 9/2014 | Mumby et al. |
| 2016/0158569 | A1* | 6/2016 | Mofar .................. A61N 5/0616 600/14 |
| 2016/0184601 | A1* | 6/2016 | Gleich .................... A61N 2/02 600/14 |
| 2016/0228721 | A1 | 8/2016 | Mohamed et al. |
| 2018/0056087 | A1 | 3/2018 | Ribeiro et al. |
| 2018/0318595 | A1 | 11/2018 | Martinez |

FOREIGN PATENT DOCUMENTS

| | | |
|---|---|---|
| DE | 199383 | 10/1906 |
| DE | 3101715 | 9/1982 |
| DE | 10332771 | 3/2005 |
| DE | 202009011054 | 3/2010 |
| DE | 102015011092 | 3/2017 |
| JP | 2006-519680 | 8/2006 |
| JP | 2009-525769 | 7/2009 |
| JP | 2015-527134 | 9/2015 |
| JP | 2016-522059 | 7/2016 |
| JP | 2017006347 | 1/2017 |
| JP | 3213328 | 11/2017 |
| JP | 3213328 U | 11/2017 |
| RU | 94003023 | 5/1996 |
| WO | 0193949 | 12/2001 |
| WO | 2008049775 | 5/2008 |
| WO | 2011089472 | 7/2011 |
| WO | 2012152234 | 11/2012 |
| WO | 2016038410 | 3/2016 |
| WO | 2016043615 | 3/2016 |

OTHER PUBLICATIONS

Wikimedia Foundation. (May 11, 2012). Mu-metal. Wikipedia. http://en.wikipedia.org/wiki/Mu-metal (Year: 2012).*
Storr, W. (Jan. 16, 2016). Bistable multivibrator or flip-flop multivibrator. Basic Electronics Tutorials. https://www.electronics-tutorials.ws/waveforms/bistable.html (Year: 2016).*
Wikimedia Foundation. (Jul. 21, 2017). Buck Converter. Wikipedia. https://en.wikipedia.org/wiki/Buck_converter (Year: 2017).*
Khatri, P. (Sep. 11, 2018). Overvoltage Protection Circuit. Circuit Digest—Electronics Engineering News, Latest Products, Articles and Projects. https://circuitdigest.com/electronic-circuits/overvoltage-protection-circuit (Year: 2018).*
European Patent Office, International Search Report and Written Opinion for International Application No. PCT/EP2019/082896, Mar. 13, 2020.
German Search Report, German Patent and Trademark Office, for DE 10 2018 009 941.6, Dec. 5, 2019.
Japanese Patent Office, Japanese Examination Report for JP Patent Application No. 2021-536359, Jun. 24, 2022.
European Patent Office, Extended European Search Report for EP 22 21 4468.5, Mar. 16, 2023.
China National Intellectual Property Administration, CN Examination Report for CN201980083990.0, Jan. 29, 2024.

* cited by examiner

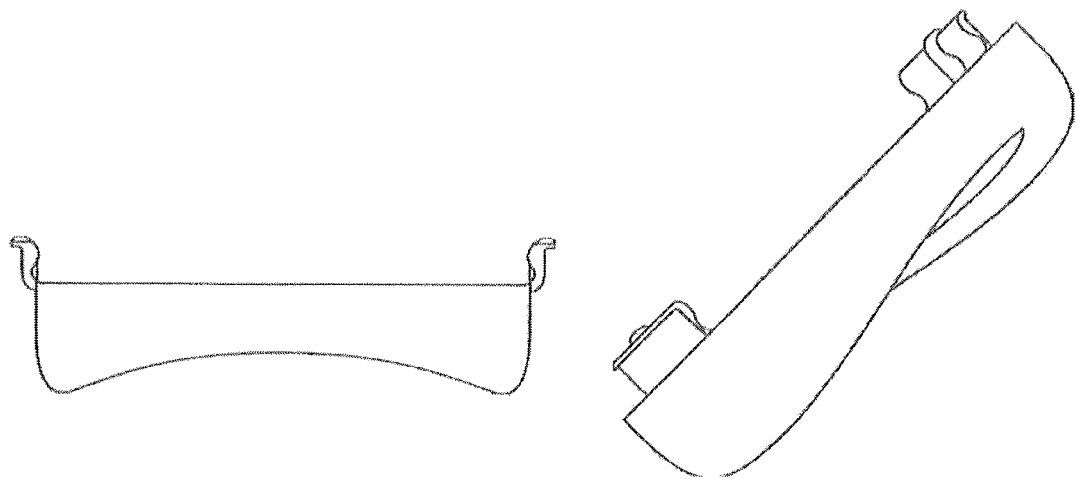
Figure 23a        Figure 23b
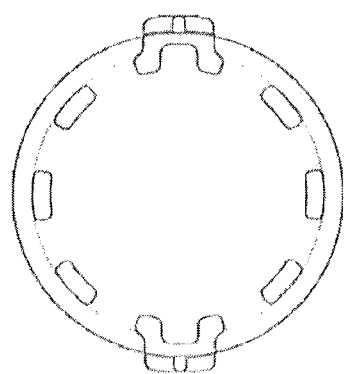
Figure 23c
Figure 23d
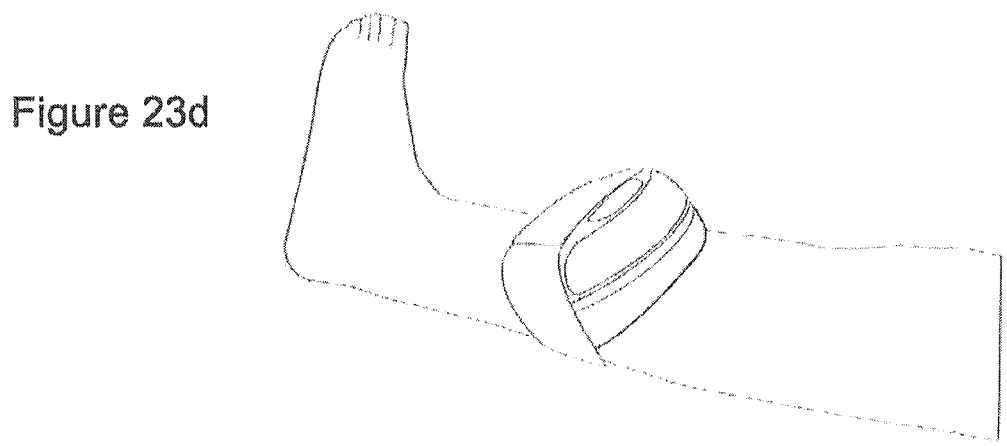

THERAPY DEVICE

CROSS-REFERENCE TO RELATED APPLICATIONS

This application is the U.S. national phase of international application PCT/EP2019/082896, filed on Nov. 28, 2019, which claims the benefit of German application DE 10 2018 009 941.6 filed on Dec. 18, 2018; all of which are hereby incorporated herein in their entirety by reference.

TECHNICAL FIELD

The present invention generally relates to a combined optical and magnetic stimulation, OMS, wound therapy device, i.e. a COMS wound therapy device via which the optical and magnetic stimulation of a wound may be performed simultaneously.

BACKGROUND

Magnetic Stimulation

The human body uses electric and magnetic signals for various physiological functions. Embryonal development, neuronal activity, polarization of cells, glandular secretion, muscle contraction, regeneration and wound healing have an electromagnetic component within all living organisms. In the recent years, tissue repair and wound healing are health care areas with the strongest growing body of evidence for beneficial usage of electric and magnetic stimulation. At the core of its transduction mechanism, electric fields are generated through flow of ionic currents across tissue layers and cell membranes. Any electric current induces a magnetic field and vice versa.

The epidermal skin layer is mainly composed of polarized epithelial cells and keratinocytes. The majority of Na+ channels are located at the apical membrane and the majority of K+ channels and Na+/K+ ATPase pumps at the basolateral membrane. This distribution of ion channels leads to a transepidermal ion flow from the apical side to the basal side, returning at paracellular spaces between epidermal cells. This flow of ions generates a voltage gradient across the epidermis which is called the transepidermal potential (TEP). About half of the cellular energy source ATP, provided through mitochondrial respiration, is used to generate such ion concentration gradients to build up potential differences across cell membranes (membrane potential, 70 mV) or cell layers (transepithelial potentials, 30 to 100 mV).

In healthy dermal layers, the TEP is proportional to the resistance of the ion flux between epidermal cells through the paracellular pathway, typically between 15-60 mV. In case tight junction resistance is reduced or skin integrity is lost in dermal lesions, the flow of ions follows the low resistance pathway, generating a lateral electric field gradient. The electric field is sensed by the cells in the wound microenvironment and initiates biological responses such as proliferation and migration of endothelial cells and keratinocytes leading to enhancement of reepithelization and hence support the wound healing progress. This current of injury can be considered as a driving factor for complex biological mechanism in regeneration. As soon as the epidermal layer is restored, the surface potential declines and the TEP is re-established.

Healing of the injured tissue is arrested or will be incomplete if reduced or no current is sensed by cells in the surrounding tissue. Under ischemic conditions, reduced vascular supply limits the cellular ATP production and therefore the ability to maintain an adequate TEP. Consequently, no current of injury can establish upon lesion and the electric signal for cells at the wound edge to re-induce tissue regeneration is lost. Feigning the natural current of injury, therefore becomes a promising rational to induce and/or promote wound healing in chronic wounds. The aim of the magnetic stimulation according its mechanism of action is to stimulate the biological target only temporary and achieve a lasting effect.

Whereas static magnetic fields only exert forces on moving charges, time varying fields exert a force on resting charge carriers as well. Magnetic fields penetrate through tissue, thereby exerting various biological responses in organisms. Alternating electric currents as they are produced by neuronal activity or piezoelectric mechanisms, generated by movements of muscles, joints, bones, tendons or vibrating protein structures, produce pulsed characteristics of magnetic fields. These time varying character of magnetic fields are much more subtle in living organisms compared to static magnetic fields. Bodily tissue is able to sense and respond to electric and magnetic stimuli from external sources. The frequency and amplitude and of external stimulation is crucial to determine the outcome and extent of biological and physiological responses. Induction of electric currents in the body can be achieved through inductive coupling, by exposing the area of concern to time varying magnetic fields.

Optical Stimulation

Photobiomodulation or optical stimulation is a phenomenon that describes the biological responses upon irradiation with light. Light is absorbed by chromophores in biological systems. Photomodulative properties are found among photoactive porphyrins, hemoglobin, melanin, flavoproteins, NADH dehydrogenase, glutamate dehydrogenase, flavin, retinols, RNA and DNA, phosphatidylinositol and adenosintriphosphate. The photo-receptive capacity of chromophores, arises from the molecular substructures, capable for electronic excitation upon exposure to specific ranges of the electromagnetic spectrum. Electronically excitable properties are attributed to conjugated pi-electron systems, metallic complexes and Fe—S clusters, which all are able to form resonance isoforms upon absorption of specific bands within the EM spectrum. Change of electronic excitation upon light absorption, is the primary mechanism by which biological responses are triggered on a molecular level. Electronic transitions as they are found during oxidation or reduction of metallic centers in protein substructures, allow conformational changes to occur. Triggering of these phase transitions in the active center along the chain of catalytic chemical reactions, can facilitate the substrate to product conversion and improves the overall kinetic turnover rates of the enzymes. Taking under consideration the various relevant involvement of enzymes in living cells, creates a rational to focus on the absorption of light by photoreceptive molecular structures with enzymatic activity.

The "optical window" is defined as a relatively narrow range of wavelengths which interact with biological photoacceptors. Water in the body significantly absorbs wavelengths larger than 1100 nm. Wavelength shorter than 600 nm are predominantly absorbed by oxyhemoglobin and melanin. Therefore, tissue penetration for optical illumination is maximized between 600-1000 nm. The irradiation in the far red to near infrared spectral range (630-1000 nm) using low energy light emitting sources is reported to be especially bio-modulative in cell cultures and animal models. This spectral range represents an optical window for biologic stimulation.

Cytochrome C oxidase was identified as a key photoreceptor in the far red to near-infrared range of the electromagnetic spectra, detectable in vivo by near-infrared spectroscopy. COX is an integral membrane protein in the inner mitochondrial membrane, with catalytic activity, responsible for cleavage of oxygen in the mitochondrial respiratory chain. As am hemeprotein, COX contains two iron (HemeA and HemeB) and two copper centers (CuA and CuB) at its active site. The different redox states of the enzyme correlate with the four wavelength ranges for maximal absorption at 613.5-623.5 nm, 667.5-683.7 nm, 750.7-772.3 nm and 812.5-846.0 nm and was proposed as primary photo acceptor for optical stimulation.

Combined Optical and Magnetic Stimulation

The two treatment modalities are based on utilization of specific frequency ranges of the electromagnetic spectra. Despite similar in its electromagnetic nature, both entities greatly differ in their physical characteristics and mode of action when interacting with living tissue. Whereas magnetic stimulation enables the induction of electric currents in the wound environment in order to re-establish a wounds normal electrophysiological properties, optical stimulation targets the electron transfer rates in the active center of enzymes in the respiratory chain to augment cellular regeneration capacity in the wound bed. Each intervention (OS & MS) and its respective target (wound bed or wound environment) has its relevance as standalone in order to support the complex process of wound healing. The two treatment modalities and the different underlying mechanisms of interaction are supposed to complement each other to create physiologically synergistic effects and are therefore both implemented in the medical device. As a matter of fact, no other pre-clinical model would serve as reasonable enough to distinguish the effects arising from single or combined application of optical and magnetic stimulation, as this is linked to the chronicity of pathologically disturbed human tissue. The combined optical and magnetic stimulation does not replace any standard of care procedures, but covers an additional range of interventional measures necessary to achieve a holistic treatment approach with respect to the patient's diverse medical need.

An object of the present invention is to provide an improved device which offers a non-invasive and non-toxic therapeutic approach for wound healing.

SUMMARY

The invention is set out in the independent claim. Preferred embodiments of the invention are outlined in the dependent claims.

According to a first aspect of the present disclosure, we describe an optical and magnetic stimulation, OMS, wound therapy device (i.e. a COMS wound therapy device) comprising: a light source configured to generate an optical field for an OMS wound therapy; an electric circuit coupled to the light source for driving the light source to generate the optical field; a coil configured to generate a magnetic field for the OMS wound therapy; and a magnetic field shield arranged between the coil on the one hand and the light source and electric circuit on the other hand, and wherein the magnetic field shield is configured to shield the electric circuit and the light source from the magnetic field generated by the coil.

The device may, according to some example implementations as described herein, combine the technologies of magnetic stimulation and photon emission applied locally to a wound area of a patient.

Providing a magnetic field shield between the coil on the one hand and the light source and electric circuit on the other hand may allow for homogenization of the magnetic field distribution. This may be particularly important when aiming to homogenize the magnetic field in a therapeutic application, for example for different localizations and/or indications. This may allow for more precisely controlling the (treatment) magnetic field to which the wound of the patient is to be exposed.

When combining magnetic stimulation and photon emission technologies, it may be necessary to provide the light source (which may, for example, be one or more LEDs) and the electric circuit coupled to the light source for driving the light source to generate the optical field close to the coil to provide a compact OMS wound therapy device. Magnetic fields may hereby induce eddy currents on the electric circuit (which may, for example, be a printed circuit board) which could disturb the complete electric circuit.

It is to be noted that any references to the combined optical and magnetic stimulation wound therapy device used throughout the present disclosure may refer to optical and magnetic stimulation/treatment fields being generatable simultaneously.

The magnetic field shield according to some example implementations of the device as described herein, however, allows for a compact design of the OMS wound therapy device, while reducing the impact of the magnetic field on the electric circuit. At the same time, as outlined above, the magnetic field shield may further allow for providing a homogeneous magnetic field, for example according to some example implementations of the device as described herein for a distance of up to 40 mm from the coil or even further than 40 mm away from the coil, as will be outlined in more detail below. The magnetic field strength generated up to a certain distance from the coil may further be increased by using the magnetic field shield compared to a device in which no magnetic field shield is used.

In particular by increasing the magnetic field strength and allowing the device to be prepared in a more compact manner, the magnetic field shield may at the same time make the device more efficient, in particular as the device may be less heavy, less energy consuming and less heating may be produced when the device is being used. The compact and portable design of the device may further help ensuring easy application and efficiency of the wound therapy.

In some example implementations, the magnetic field shield may be a thin (for example between 0.1 and 5 mm thin) sheet. Additionally or alternatively, the magnetic field shield may be made of a Mu-metal (for example nickel-iron soft ferromagnetic alloy) which may be particularly suitable for shielding the electric circuit and the light source from the magnetic field generated by the coil.

It is to be noted that the coil may be driven by the same electric circuit which is used to drive the light source. Additionally or alternatively, the coil may (also) be driven by a different electric circuit. If the same electric circuit is used for driving the light source and the coil, the magnetic field shield may, in some examples, comprise openings for guiding the wire of the coil through the magnetic field shield.

In some examples, the OMS wound therapy device is configured to generate, using the coil and the magnetic field shield, an attenuated magnetic field, on a side of the magnetic field shield on which the electric circuit and light source are arranged, to induce, based on the attenuated magnetic field, an eddy current in a layer of the OMS wound therapy device on or which the electric circuit is arranged. This may be particularly advantageous as the eddy current may generate a further magnetic field which is inversely polarized to the (treatment) magnetic field for the OMS wound therapy referred to above, so as to further reduce the impact of the treatment magnetic field on the electric circuit (and other electrical components on that side of the magnetic field shield opposite to the side of the magnetic field shield on which the coil is arranged). The magnetic field being attenuated hereby means that the magnetic field is attenuated on the side where the light source and electric circuit are arranged compared to the magnetic field which is produced via the coil on the side of the magnetic field shield where the coil itself is arranged.

In some examples of the OMS wound therapy device, the magnetic field shield comprises a material having a relative magnetic permeability of more than 5000, preferably more than 10000, more preferably more than 20000, and more preferably more than 50000 (measured in units of the permeability of free space $\mu_0$). The magnetic field shield may hereby, for example, be made out of or comprise a Mu-metal shield. Providing a material having such high relative magnetic permeability may allow for efficiently shielding the electric circuit and light source from the magnetic field generated by the coil. Further still, a homogeneous magnetic field may hereby be provided up to a certain distance (for example up to 40 mm or more) from the coil by using a material having such high relative magnetic permeability.

In some examples of the OMS wound therapy device, the magnetic field shield comprises one or more magnetic field shield openings through which the optical field can penetrate for irradiating a wound of a patient. The components (for example one or more LEDs) of the light source may hereby be arranged in the OMS wound therapy device such that their location essentially corresponds to the magnetic field shield opening(s) so as for the optical field being able to efficiently penetrate the (e.g. layer of the) magnetic field shield, in particular to further homogeneous exposure of the wound of a patient to the optical field.

In some examples of the OMS wound therapy device, the magnetic field shield comprises one or more side walls configured to prevent the magnetic field from penetrating through to the electric circuit and the light source via an edge or corner region of the magnetic field shield. This may be particularly advantageous insofar that the (treatment) magnetic field can be further confined to provide a more homogeneous and stronger (treatment) magnetic field to which the wound of the patient is exposed. At the same time, the eddy current generated on the side of the magnetic field shield on which the electric circuit and light source are arranged can be better controlled, in order to minimize the influence of the treatment magnetic field on the electric circuit.

In some examples, the OMS wound therapy device comprises a coil voltage supply coupled to a bridge coil driver for driving the coil to generate a pulsed modulated magnetic field. A homogeneous magnetic field may hereby be generated with pulses having, for example, a trapezoidal shape in time.

In some examples of the OMS wound therapy device, the bridge coil driver comprises a first transistor configured to prevent a current from flowing back to the coil voltage supply during a falling edge of a pulse (having, for example, a trapezoidal shape) of the pulsed modulated magnetic field.

In some examples, the bridge coil driver comprises a linear current regulator comprising a second transistor, wherein the second transistor is coupled with the first transistor, and wherein the bridge coil driver is configured, based on the current being prevented, via the first transistor, from flowing back to the coil voltage supply during the falling edge of the pulse, to induce a rising voltage on the second transistor during the falling edge of the pulse. This may lead to a fast decay of the energy stored in the coil, which may be advantageous so as to be able to provide defined pulses of the pulsed modulated magnetic field, while the magnetic field is homogeneous up to a certain distance from the coil at the same time, as outlined above. This may allow for more precisely controlling the (treatment) magnetic field to which the wound of the patient is to be exposed.

In some examples of the OMS wound therapy device, the bridge coil driver further comprises a Zener diode coupled with the first and second transistors, and wherein the Zener diode is configured to prevent the first and second transistors to be damaged due to an overvoltage during a switch-off of the bridge coil driver. Such an overvoltage may in particular occur during a switch-off of the low-side drivers of the bridge coil driver. The Zener diode may therefore in particular enable using the transistors as outlined above so as to allow for a fast decay of the energy stored in the coil for increased precision of controlling the (treatment) magnetic field to which the wound of the patient is to be exposed.

In some examples, the OMS wound therapy device further comprises a coil supply voltage control filter and a buck converter coupled to the coil voltage supply for adjusting an output voltage of the coil voltage supply. The pulse width modulated signal, which may be low-pass filtered, may be fed into the feedback network of the buck converter which may allow adjusting the output voltage of the coil supply, in some examples, from 0.7 V to 3.2 V. This may allow for increasing the coil supply voltage, which may be necessary in some examples in order to reach a high di/dt (i.e. current increase in time) of the inductive coil during fast-rising slopes of the, for example, trapezoid signal. In some examples, after the slope, the voltage may be reduced to increase efficiency of the coil driver.

In some examples, the Coil Supply Voltage Control PWM Filter directly controls the Coil Supply/Buck Converter's output voltage in the range of, for example, 0.7 V-3.2 V, which in turn may power the Full Bridge Coil Driver.

The Full Bridge Coil Driver may control the current through the coil with a linear current regulator implemented in the lower side of the Full Bridge Coil Driver by acting as a variable resistor that may convert excess energy into heat. Higher voltage on the Full Bridge Coil Driver may therefore mean higher energy dissipation in the linear current regulator.

Faster current changes (higher di/dt) in the coil may require higher voltages applied to the coil in order to be able to enforce these current changes. Therefore, in order to minimize energy consumption during slow or no current changes, the Full Bridge Coil Driver's supply voltage can be reduced, in some examples, to an appropriate level via the Coil Supply Voltage Control PWM Filter.

The above may allow precisely defining the rising slope of the pulsed width magnetic field signal so as to increase precision for controlling the (treatment) magnetic field to which the wound of the patient is to be exposed.

Example implementations of the OMS wound therapy device as outlined above may allow for providing a fast increase and decrease of the pulse for improved control of the (treatment) magnetic field, in particular as the magnetic field exposure of the wound can be controlled more precisely.

In some examples of the OMS wound therapy device, the light source comprises a plurality of LEDs, and wherein a layer of the OMS wound therapy device on which the LEDs are arranged is split into a plurality of segments, wherein each of the segments comprises one or more of the plurality of LEDs. The layer device on which the LEDs are arranged may, for example, be split in eight segments. Splitting the layer into segments may result, on the one hand, in spreading the heat from the LEDs and, on the other hand, in the layer acting as an additional shield from magnetic fields.

The magnetic field may hereby induce an opposing magnetic field in the LED heat sinks which may help protecting the GND plane on the inner layers. The heat sinks may be kept as large as possible to optimize protection. Additionally or alternatively, the GND plane may be split into two parts (which may be connected in the middle) to further divide the influence of the residual magnetic field.

In some examples of the OMS wound therapy device, the coil is wound to comprise openings at locations corresponding to respective locations of the LEDs to allow penetration of the optical field through the coil. This may advantageously allow for preventing field disturbance and avoiding reduced efficiency of penetration of the optical field through the coil towards the wound of the patient. The geometry in which the coil is wound to comprise openings allows for further optimizing homogenization of the (treatment) magnetic field in particular within a therapy distance and/or area, while allowing the therapy optical field to penetrate the coil.

In some examples of the OMS wound therapy device, the coil is wound to have a substantially annular shape, and wherein the openings are arranged at a gap region which is provided between a first radial location of the coil comprising a first loop and a second radial location of the coil comprising a second loop. The different coil parts (including loops) may hereby, in some examples, only be connected at a single azimuthal angular position of the coil, as will be further described below. As outlined above in relation to the coil being wound to comprise openings at locations corresponding to respective locations of the LEDs, the geometry of the gap allows for further optimizing homogenization of the (treatment) magnetic field, while allowing the therapy optical field to penetrate the coil.

In some examples, the OMS wound therapy device further comprises a distance sensor configured to determine whether a surface is within a predefined distance to the OMS wound therapy device, and wherein the OMS wound therapy device is configured to generate one or both of the optical field and the magnetic field only if the surface is within the predefined distance to the OMS wound therapy device, and in particular the light source and the coil. This may allow for the device targeting a surface (usually the skin of the patient) if it is attached and/or mounted properly. Furthermore, using the distance sensor helps ensuring that the wound is exposed to a uniform magnetic field based in particular on a distance of the wound from the coil for which the shape and strength of the magnetic field can be very precisely controlled in particular using example implementations of the device as outlined above and below.

In some examples, the OMS wound therapy device further comprises an optical sensor configured to detect one or more of: an amount of light reflected from a surface; a color of the surface (wherein the OMS wound therapy device may be configured to correlate the color of the surface with a color code for a wound stored in a memory of the OMS wound therapy device); a surface structure of the surface (wherein the OMS wound therapy device may be configured to correlate the surface structure with a surface structure for example of a wound, stored in the memory of the OMS wound therapy device); and a reflection and/or scattering parameter of the surface; and wherein the OMS wound therapy device is configured to determine, based on one or more of the amount of light reflected from the surface, the color of the surface, the surface structure of the surface and the reflection and/or scattering parameter of the surface, whether the surface belongs to a wound, and wherein the OMS wound therapy device is configured to generate one or both of the optical field and the magnetic field only if the surface is determined to belong to a said wound. The comparison between the detected amount of light reflected from the surface and/or color of the surface and/or surface structure of the surface and/or reflection and/or scattering parameter of the surface may be compared to data stored in the OMS device itself, or it may be compared internally or externally to data which may be stored in an external memory.

It is to be noted that in any one or more of the examples as outlined throughout the present disclosure, the optical sensor may be comprised in or be the same as the distance sensor. Therefore, any properties and functionalities of the optical sensor may equally be applicable to the distance sensor, and vice versa.

In some examples, the OMS wound therapy device further comprises an accelerometer, and wherein the OMS wound therapy device is configured to: determine, via the accelerometer, whether the OMS wound therapy device is placed on an unlively (i.e. static) object (for example a table or other surface not belonging to a patient to be treated), and if the OMS wound therapy device is determined to be placed on a said unlively object, prevent the optical field and/or the magnetic field from being generatable. This may improve longevity of the device in particular when it is battery-driven.

In some examples, the OMS wound therapy device further comprises a flexible consumable for attaching the OMS wound therapy device to a wound of a patient, and wherein a distance between a said wound and the light source and the coil, respectively, is adjustable by varying a depression state of the flexible consumable. As will be appreciated, the distance between the wound and the light source and the distance between the wound and the coil may be varied simultaneously, since the coil and the light source are both fixed together in a non-consumable part of the device.

The device may hereby be fixed to the body part of the patient at a particular depression state, for example using a strap or other fixation device. Providing a flexible consumable allows for easy adjustment of the distance of the light source and the coil, respectively, to the wound to be treated, which may allow in particular exposing the wound to a magnetic field at a location for which the magnetic field can be precisely controlled (homogenous magnetic field, strength of the magnetic field). Equally, the optical field exposure of the wound can be varied in a very precise manner.

In some examples, the flexible consumable is configured to conform to a shape of a body part of the patient to which the OMS wound therapy device is to be attached. This may further improve exposing the wound to a magnetic field at a location for which the magnetic field can be precisely controlled (homogenous magnetic field, strength of the magnetic field), in particular irrespectively of the particular shape of the body part of the patient where the wound is to be treated.

In some examples, the OMS wound therapy device comprises a non-consumable part which comprises the light source, the electric circuit, the coil and the magnetic field shield, and wherein the OMS wound therapy device is configured to provide an audible feedback when the consumable is attached to the non-consumable part. Correct attachment of the consumable to the non-consumable part may hereby be ensured, which allows in particular precisely controlling the magnetic and optical fields (in particular in view of the distance between the coil and the light source, respectively, and the wound) to which the wound is exposed.

In some examples, the flexible consumable has a substantially ring shape and/or wherein the flexible consumable is translucent to the optical field. The consumable may therefore not only allow for improved control of exposing the wound to the magnetic and optical fields, but also helps preventing the consumable from detrimentally affecting the wound from being exposable to the optical field.

In some examples, the flexible consumable is configured to be attachable to a said wound based on a pressure-reduced attachment mechanism. Easy fixation of the OMS wound therapy device to the patient may hereby be ensured so as to allow, in particular, precisely controlling the magnetic field to which the wound is to be exposed. The pressure-reduced attachment so as to conform to the anatomy of the patient may hereby comprise a spring shape and/or a cylindrical fit shape.

In some examples of the OMS wound therapy device, the light source is configured to emit light having a wavelength of approximately 660 nm and/or 830 nm. A wavelength at 660 nm and 830 nm was found to advantageously trigger the electronic phase transitions in the active center (or active part) of the mitochondrial cytochrome C oxidase, which facilitates the substrate to product conversion and improves the overall kinetic turnover rate of the enzyme.

Additionally or alternatively, in some examples of the OMS wound therapy device, the light source is configured to emit light having a wavelength between approximately 400 nm and 430 nm. A wavelength of 400-430 nm was shown to advantageously induce an increase in reactive oxygen species (ROS). While certain concentrations of free radicals may be capable of stimulating cell signaling and gene expression in eukaryotes, blue light (in particular at a wavelength of 400-430 nm) was found to have toxic effects on bacteria, which are due to lower levels of antioxidants much more sensitive to ROS.

In particular, in prokaryotic cells it was shown that a wavelength of 400-430 nm excites naturally occurring endogenous photosensitizing chromophores (iron-free porphyrins and flavins) which may lead to the production of cytotoxic ROS. In Eukaryotic cells it was shown to induce an increase in intracellular ROS by excitation of flavins within the peroxisomes and mitochondria of mammalian cells. The redox potential may be shifted towards oxidation which was found to advantageously have stimulatory effects on cell signaling and gene expression.

BRIEF DESCRIPTION OF THE DRAWINGS

These and other aspects of the present disclosure will now be further described, by way of example only, with reference to the accompanying figures, wherein like reference numerals refer to like parts throughout, and in which:

FIGS. 23a to d show schematic illustrations of a consumable according to some example implementations as described herein.

DETAILED DESCRIPTION

Figure 1:
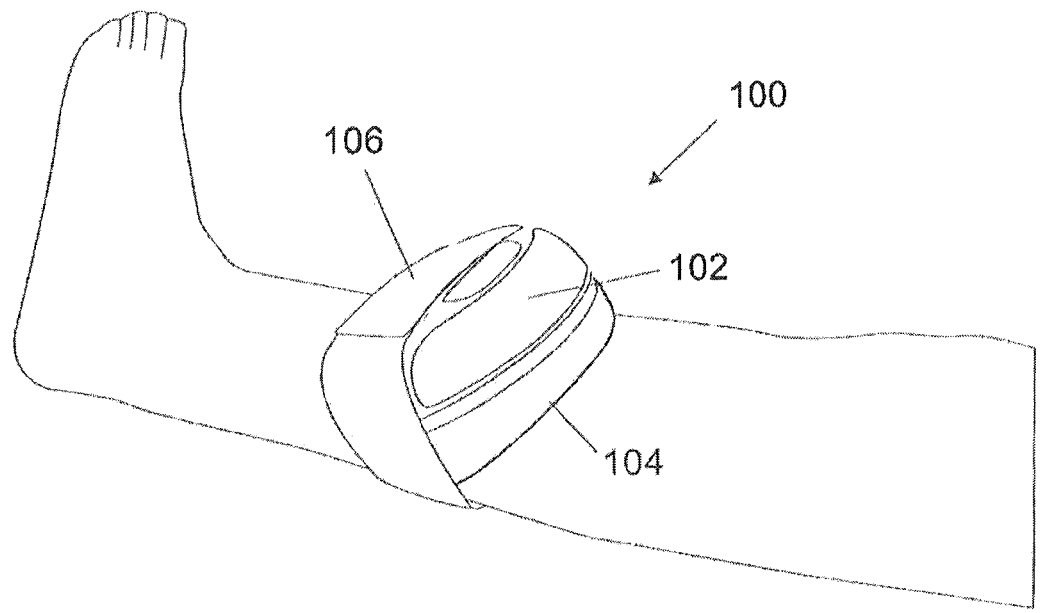
FIG. 1 shows a photographic image of an OMS wound therapy device according to some example implementations as described herein.

FIG. 1 shows a photographic image of an OMS wound therapy device 100 according to some example implementations as described herein.

In this example, the OMS wound therapy device 100 comprises a non-consumable part 102 and a consumable 104, which is, in this example, a flexible consumable.

In this example, the OMS wound therapy device 100 is fixed to a body part (for example a leg) of the patient using a strap 106.

Figure 2:
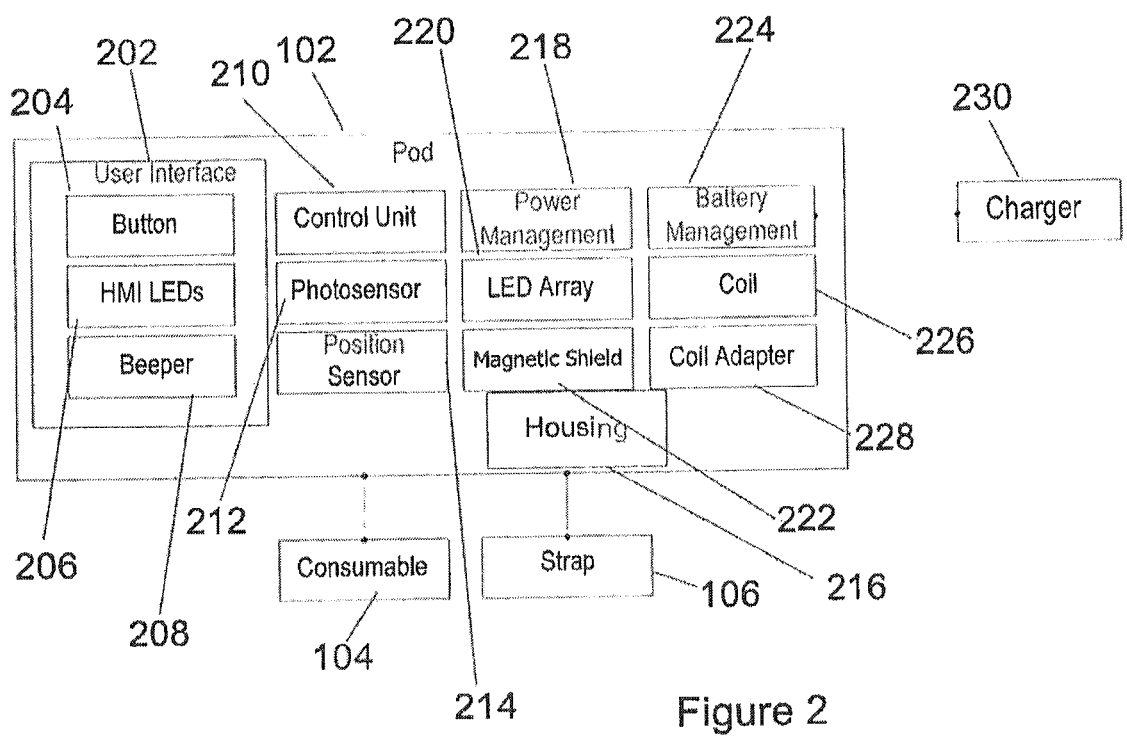
FIG. 2 shows a schematic block diagram of an OMS wound therapy device according to some example implementations as described herein.

FIG. 2 shows a schematic block diagram of an OMS wound therapy device according to some example implementations as described herein.

In this example, the OMS wound therapy device comprises a non-consumable 102 (dubbed "Pod" in FIG. 2). The non-consumable 102 refers to that part of the device which may contain all electronics.

In this example, the device further comprises a charger 230 which may contain a USB cable and a standard USB charging device.

Furthermore, in this example, the device further comprises a coil 226 which is configured to generate a magnetic field for the combined optical and magnetic stimulation (COMS) therapy.

Further still, in this example, the device further comprises a coil adapter 228. The coil adapter 228 is a mechanical holder for the coil 226.

The device of the example implementation as shown in FIG. 2 further comprises a magnetic field shield 222 which shields the electronics from the magnetic field generated by the coil 226. In this example, the magnetic field shield 222 comprises a Mu-metal sheet.

In this example, the device further comprises an LED array 220 which is configured to emit the optical field for the COMS therapy.

The device further comprises in this example a housing 216 which may incorporate and protect all pod (non-consumable part) components. It may further interface with the consumable 104 and the strap 106.

The device further comprises, in this example, a photosensor 212 which is configured to sense the intensity of the reflected light and may be used as an object presence detector. The photosensor 212 may hereby be comprised in or integral to the distance sensor and/or optical sensor as described throughout the present specification.

In this example, the device further comprises a position sensor 214 which is configured to measure a position of the non-consumable part 102. The position sensor may be a 3-axis acceleration sensor. It may be used to detect motion expected to occur when the user is wearing the device as opposed to no motion when the device is stationary (e.g. lying on a table). Activation of the therapy may be inhibited while the device is stationary (not worn by a user).

Further still, in this example, the device further comprises a user interface 202. The user interface 202 comprises a button 204 (which may be an on/off button), human machine interface (HMI) LEDs 206 which may be used to provide visual status (of, for example, an on/off/idle state of the device) feedback to the user, and a beeper 208 which may be used to provide an acoustic status feedback (of, for example, an on/off/idle state of the device) to the user.

The device further comprises, in this example, a control unit 210, a power management unit 218 and a battery management unit 224, which will be further described below.

As outlined above, the device comprises, in this example, a consumable 104 which may be a single-use, sterile part which may protect the wound from the non-consumable part 102 of the device.

The consumable 104 may be provided in a consumable packaging which may be disposed after the consumable 104 has been removed from the wound.

The strap 106 may be used to fixate the non-consumable part 102 with respect to the wound on the patient's body.

In some example implementations, the device may be charged via a USB-C port.

The housing 216 may be a waterproof and dustproof housing (such as, but not limited to IP65).

The device may hold, in some example, two batteries (for example 2×2100 mAh/ LiMnoO2) so as to allow more than 10 treatments without charging (given some treatment sequences as specified herein).

As outlined above, the device may be provided in a relatively compact manner. The device may, in some examples, have a weight of approximately 300 grams, while the outer dimensions may be, for example, 110×110×35 mm (device only), or 120×110×60 mm (including the mounted consumable).

The consumable may relate to a sterile consumable to allow for the device to be re-usable. The strap may be provided, in some examples, for a single use (per patient).

A simple design with enhanced optical and magnetic field radiation properties for treating a wound can be provided using the device as described herein. The device may therefore be used at home or at a healthcare facility. The simple use of the device allows for wound treatment of a patient being performed by a healthcare professional or, in some examples, by the patient him- or herself.

In some examples, the device may be used in order to treat a wound having a size of up to 50 $cm^2$. The diameter of the wound to be treated may hereby be up to 8 cm large. As will be appreciated, these dimensions may be varied.

The housing may, in some examples, be comprised of a plastic two-component housing with integrated human machine interface parts (such as the button 204, status lights and a gripper).

In some examples, a sealing may be provided on one or both of the top and bottom parts of the housing with a soft sealing ring.

The light sensor (which may be integral to the photosensor 212) may detect a reflection of therapy light from which it may be determined as to whether the device is placed on the patient so that the therapy may be started or resumed.

Figure 3B:
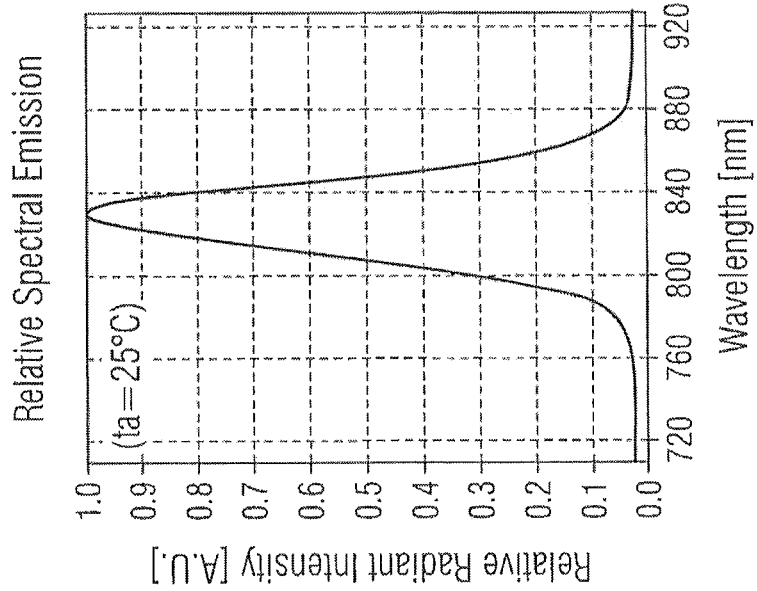
FIGS. 3a and b show relative spectral emission.
Figure 3A:
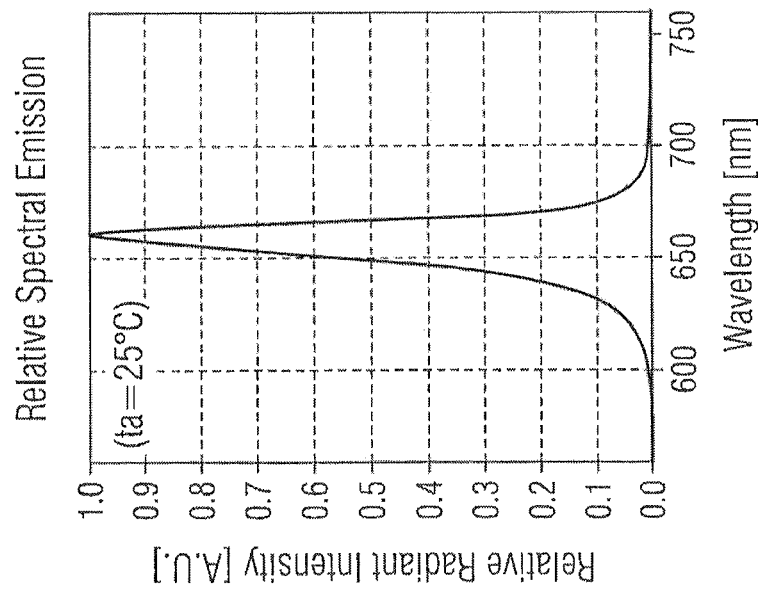

FIGS. 3a and b show relative radiant intensity (in arbitrary units) versus wavelength (in nm) for a light source, which comprises, in this example, a plurality of LEDs, according to some example implementations as described herein.

As can be seen from the relative spectral emission of FIGS. 3a and b, in this example, the LEDs comprise a central wavelength of approximately 660 nm and 830 nm, respectively. In this example, the measurements are being taken at a temperature of 25 deg C.

In this example, the device provides a peak magnetic flux density of at least 1.6 mT at the measurement point.

In this example, the device is configured to apply peak magnetic flux densities in three steps at the measurement point: at 0.4 mT (+−10%), 0.8 mT (+−10%), 1.2 mT (+−10%) and 1.6 mT (+−10%).

In this example, the device is configured to switch the polarity of the magnetic field every 2 minutes (+−1 second).

In this example, the device is configured to apply a maximum over one period of 4 $J/cm^2$ within the treatment area/distance at the brightest point.

As outlined above, the device contains in this example LEDs with manufacturers' typical peak wavelengths of approximately 660 nm and 830 nm.

In this example, the device is configured to apply light pulsed with a frequency of 1 kHz (+−2%).

In this example, the device is configured to apply an optical field over one period of 1 to 4 J/cm$^2$ within the treatment area/distance.

The magnetic field is induced, in this example, by a repetition rate of 20 Hz.

In this example, the device is configured to provide a therapy duration of 16 min (+−5 seconds).

In some examples, the device may be used on the lower leg of a patient.

In this example, the photons delivered to the wound site by the device are in the wavelength range of 650 to 670 nm and 820 to 840 nm, respectively, and are provided, in this example, via two types of LEDs. In this example, the light is pulsed at a frequency of (approximately) 1 kHz to reduce thermal effects to a minimum. In this example, the application of the optical field takes place simultaneously with the magnetic stimulation (MS) treatment, in this example, for a duration of 16 minutes, for example every second to third day during Standard of Care.

In some examples, eight LEDs are provided, although the number of LEDs may be varied. The LEDs are operated, in this example, in a pulsed mode. In this example, the pulsed mode is an alternating pulse wave. It switches between the two LED types (specified with approximately 660 nm and 830 nm, respectively) at a frequency of 1 kHz and a peak current of 350 mA (for the 660 nm LED(s)) and 650 mA (for the 830 nm LED(s)).

In this example, the duty cycles of both LEDs/LED types are between D=0.05 and 0.45 (pulse width of 5% and 45%) each. This may be adjustable to compensate any manufacturing calibration.

In this example, the total energy deposited in tissue by the device is up to and approximately 4.0 J/cm$^2$.

The switching electronics allows, in this example, for the strings of LED circuits to never be activated at the same time, so that both strings are powered by the same LED current regulator (buck converter) and operated alternately. A NOR gate is implemented in this example for two reasons: first of all, it may save a digital output on the microcontroller side and may avoid activation of both strings at the same time. Furthermore, it may increase the gate-voltage to drive the MOSFETs T10, T11 and T12 (see below). This approach may allow for reducing the RDSON of these MOSFETs significantly and may increase efficiency of the circuit. Signals may therefore not be run simultaneously even with a software update.

Figure 4A:
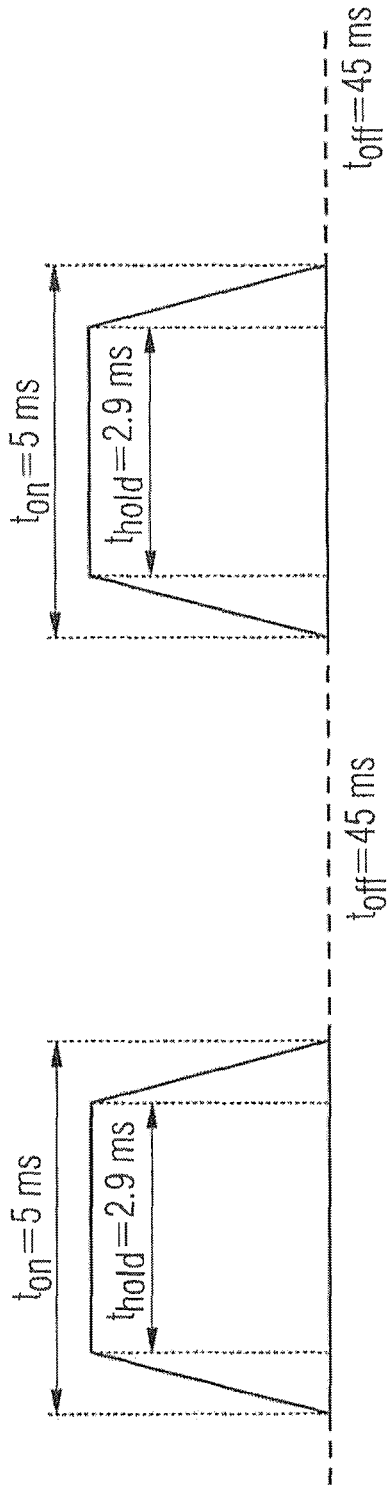
FIGS. 4a, 4b and 5 show examples of magnetic stimulation signals and sequences.
Figure 4B:
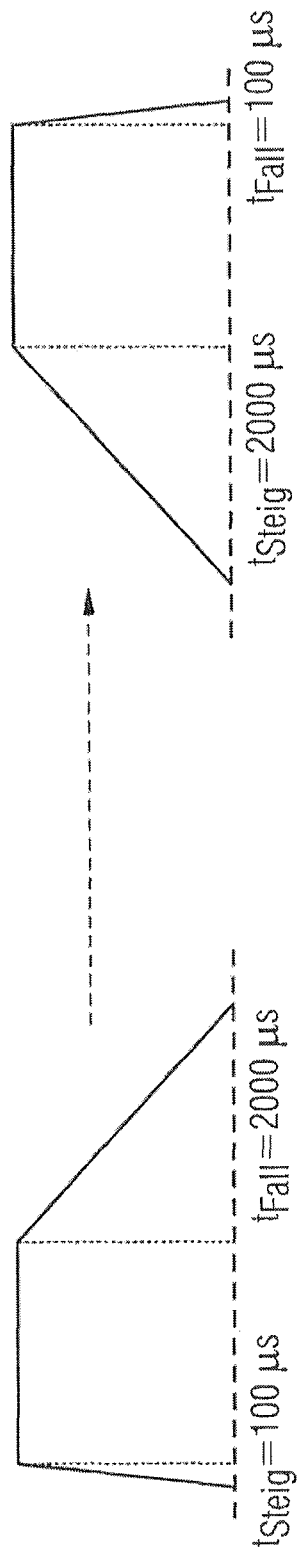
Figure 5:
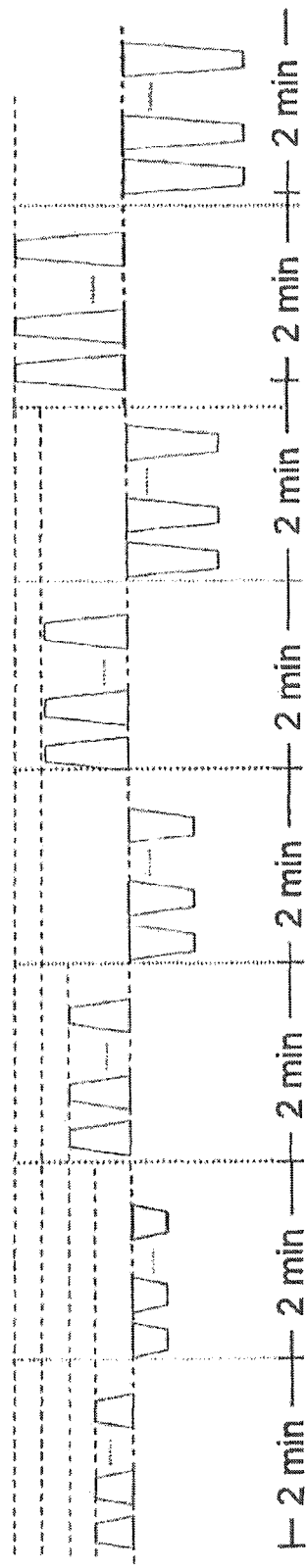

FIGS. 4a, 4b and 5 show examples of magnetic stimulation signals used in the device according to some example implementations as described herein.

The magnetic field which is generated by the device may be designed to induce currents along micro-and macro-physiological sections. Therefore, the magnetic flux density of the field may vary in time. The time varying character may be generated by bursts of trapezoidal shape. The total duration of one burst $t_{on}$ may be constant (for example 5 ms) and the time between two bursts $t_{off}$ may be constant (for example 45 ms), as shown in FIG. 4a. This example configuration results in 20 trapezoidal shaped bursts per second.

The trapezoidal bursts can be differentiated into three phases. The first phase may be characterized by a linear increase in flux density ($t_{rise}$), the second phase may comprise a constant flux density ($t_{hold}$), and during the third phase, the flux density may linearly decrease over time ($t_{fall}$). 20 trapezoidal bursts per second are, in this example, emitted by the coil. While the duration of $t_{hold}$ remains constant, the duration of $t_{rise}$ and $t_{fall}$ changes in this example from burst to burst within one second, as shown in FIG. 4b. Each second, the duration of $t_{rise}$ begins in this example at 100 µs and rises from burst to burst by 100 µs up to the last burst to 2000 µs. Complementary, $t_{fall}$ begins in this example at 2000 and decreases by 100 µs from burst to burst reaching a value of 100 µs at the last burst, as shown in FIG. 4b. This configuration results in 20 asymmetric trapezoidal shaped bursts per second.

The twenty asymmetric pulses are desired, in some examples, to compensate for the non-constant, passive dielectric properties, relative permittivity and specific conductivity, which may be caused by the heterogeneity of biological tissue. Alpha-dispersion mechanisms, which are dependent on the complex membrane surface structures, mainly arise from dynamic rearrangement of cell surface ions, shape, orientation and distribution of cells and extracellular matrix and availability of orientable dipoles and relatively free charges. These tissue properties may affect the induced current density and pathway in a frequency dependent manner. The variations in dielectric characteristics of biological tissue at various frequencies is, in some examples, the reason for choice of a relatively homogenous distribution of subharmonics most dominant between, for example, 0-300 Hz, which may be achieved by applying trapezoidal bursts with asymmetric distribution in $t_{rise}$ and $t_{fall}$.

The above described example signal configuration may be applied for 4 minutes with a maximal flux density value of 0.4 mT, whereas the polarity of the magnetic field switches after 2 minutes. For the next 4 minutes, the maximal flux density rises in this example up to 0.8 mT, again switching the polarity of the magnetic field after 2 minutes. In this manner, the signal continues for the next 4 minutes in this example with a maximal flux density of 1.2 mT and for another 4 minutes with a maximal flux density of 1.6 mT. Again, the polarity of the magnetic field switches in this example after 2 minutes to prevent habituation effects. The sequence described above is shown in FIG. 5. It will be appreciated that other sequences are possible.

Figure 6A:
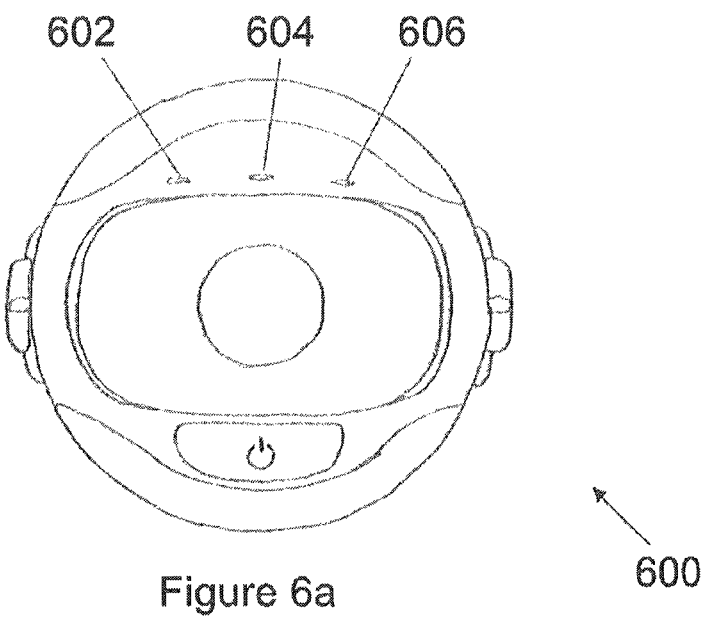
FIGS. 6a and b show schematic illustrations of the device according to some example implementations as described herein.

FIGS. 6a and b show schematic illustrations of visible elements of the device according to some example implementations as described herein. The device may correspond to the device 100 as outlined above.

As depicted in FIG. 6a, the device 600 comprises in this example a status LED system 602 to indicate the operating status of the device 600. Furthermore, in this example, the device 600 comprises a status LED temperature indicator 604 to indicate a temperature of the device while the device is in the on or idle state. Further still, in this example, the device 600 comprises a status LED battery 606 in order to indicate a battery status of the device 600.

Figure 6B:
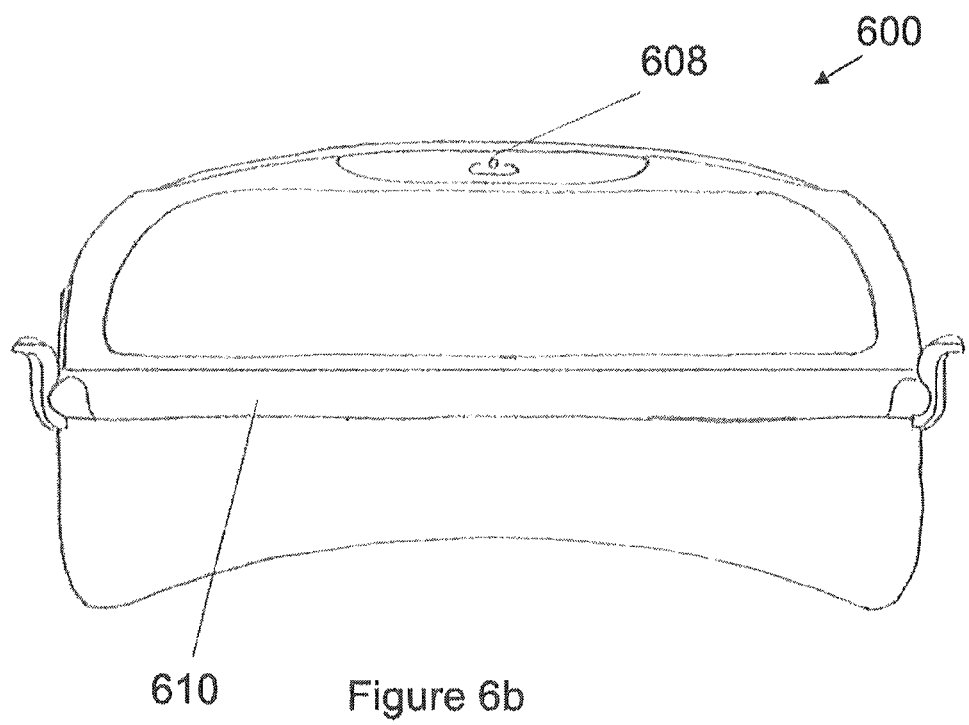

As depicted in FIG. 6b, the device 600 comprises in this example an on/off button LED 608 to indicate whether device 600 is switched on or off. Furthermore, in this example, the device 600 comprises progress bar LEDs 610 which may, in some examples, indicate the current time point of the duration of a wound treatment session given a specific sequence for the individual treatment. Further still, the device 600 comprises, in this example, therapy LEDs (not shown).

Figure 7:
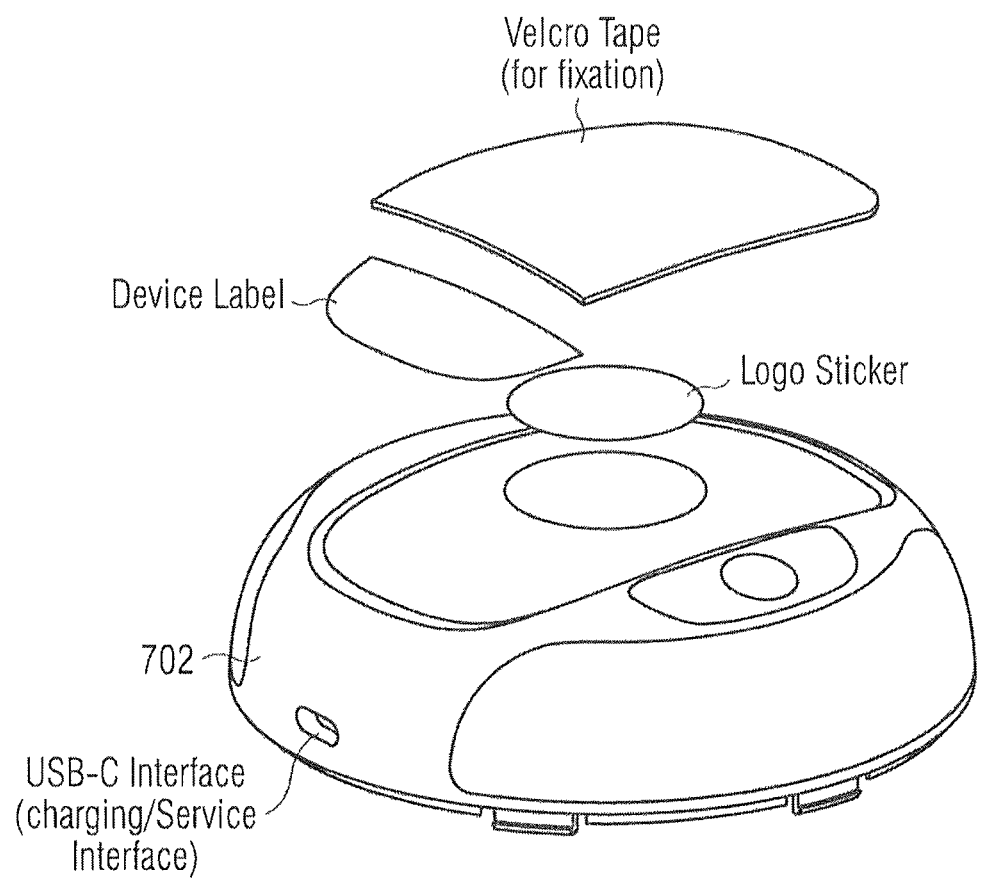
FIG. 7 shows a schematic illustration of parts of the device according to some example implementations as described herein.

FIG. 7 shows a schematic illustration of parts of the device according to some example implementations as described herein.

In this example, the device comprises a USB-C interface 702 which may be used for charging the device and/or providing other services, such as software updates or providing other data to the device, for example to provide a driving sequence to drive the device for the therapy. A Velcro tape is provided in this example for fixation purposes of the device to the patient.

Figure 8:
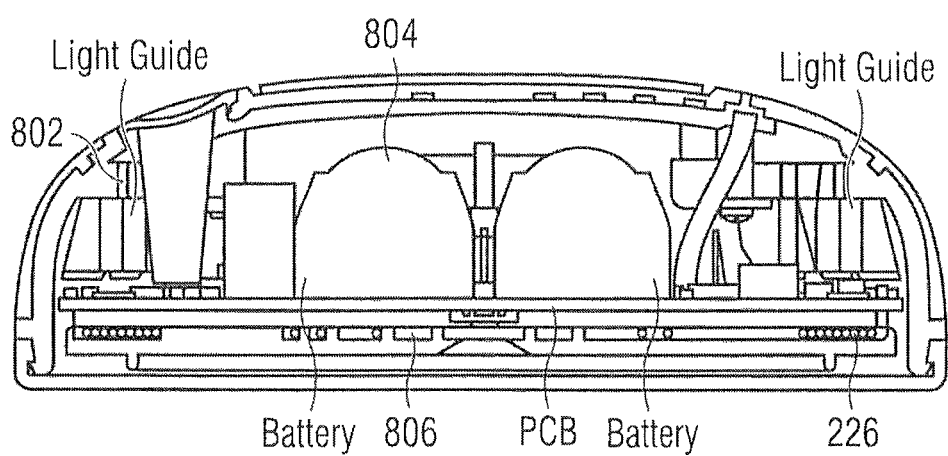
FIG. 8 shows a schematic cross-sectional side view of the device according to some example implementations as described herein.

FIG. 8 shows a schematic illustration of a cross-sectional side view of the device according to some example implementations as described herein.

In this example, the device comprises light guides 802, a battery (or multiple batteries) 804 and an electric circuit in this example in the form of a printed circuit board 806. The coil 226 is indicated in FIG. 8 as well.

Figure 9:
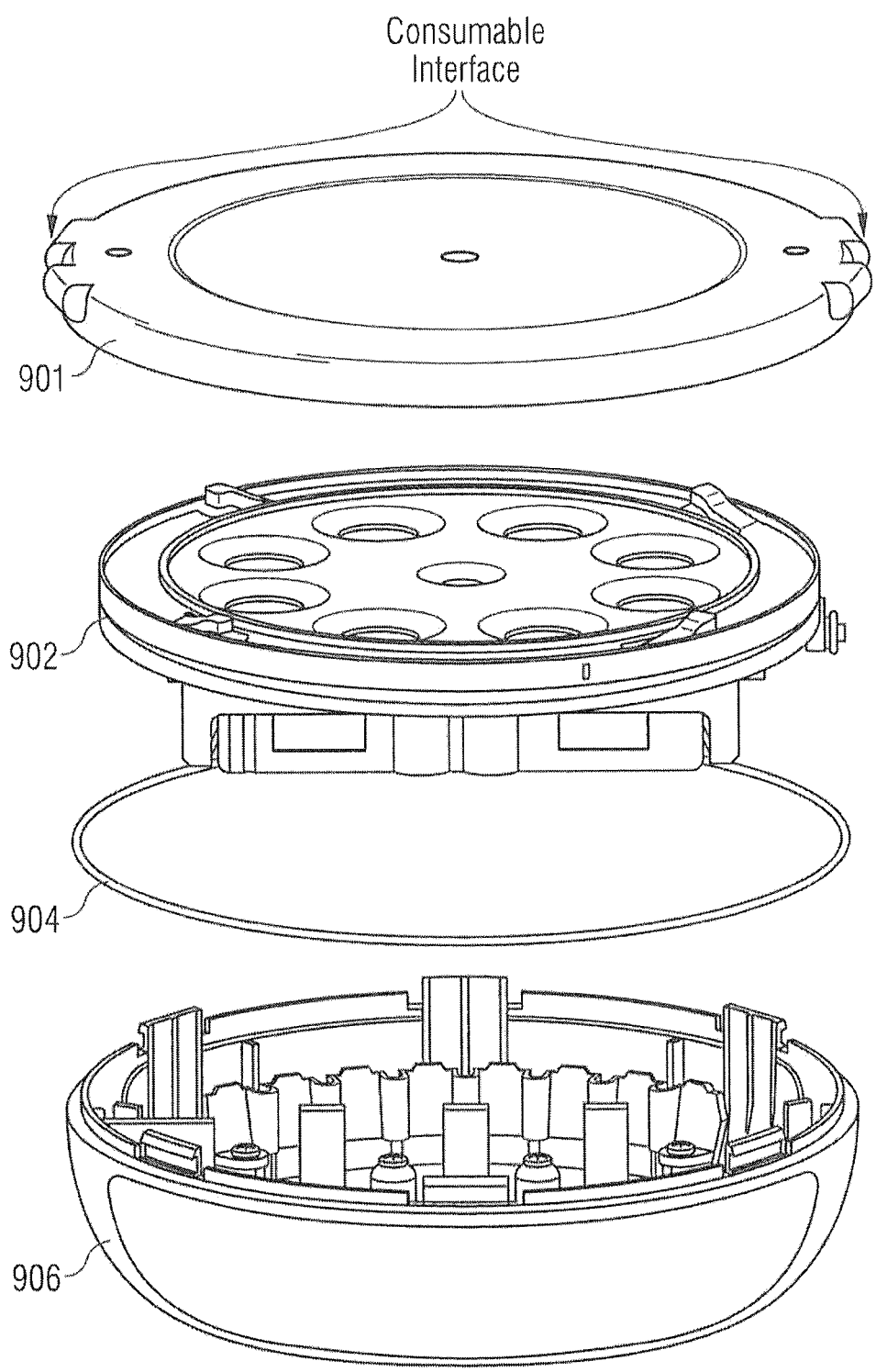
FIG. 9 shows a schematic illustration of a device according to some example implementations as described herein.

FIG. 9 shows a schematic illustration of a device according to some example implementations as described herein in a dismantled state.

In this example, the device comprises a consumable interface which may be used for connecting the consumable to the non-consumable part of the device.

In this example, the electronics assembly 902 is arranged between the housing bottom assembly 901 and the housing top assembly 906. An O-ring 904 is used in this example for arranging the electronics assembly 902 within the housing top assembly 906.

Figure 10:
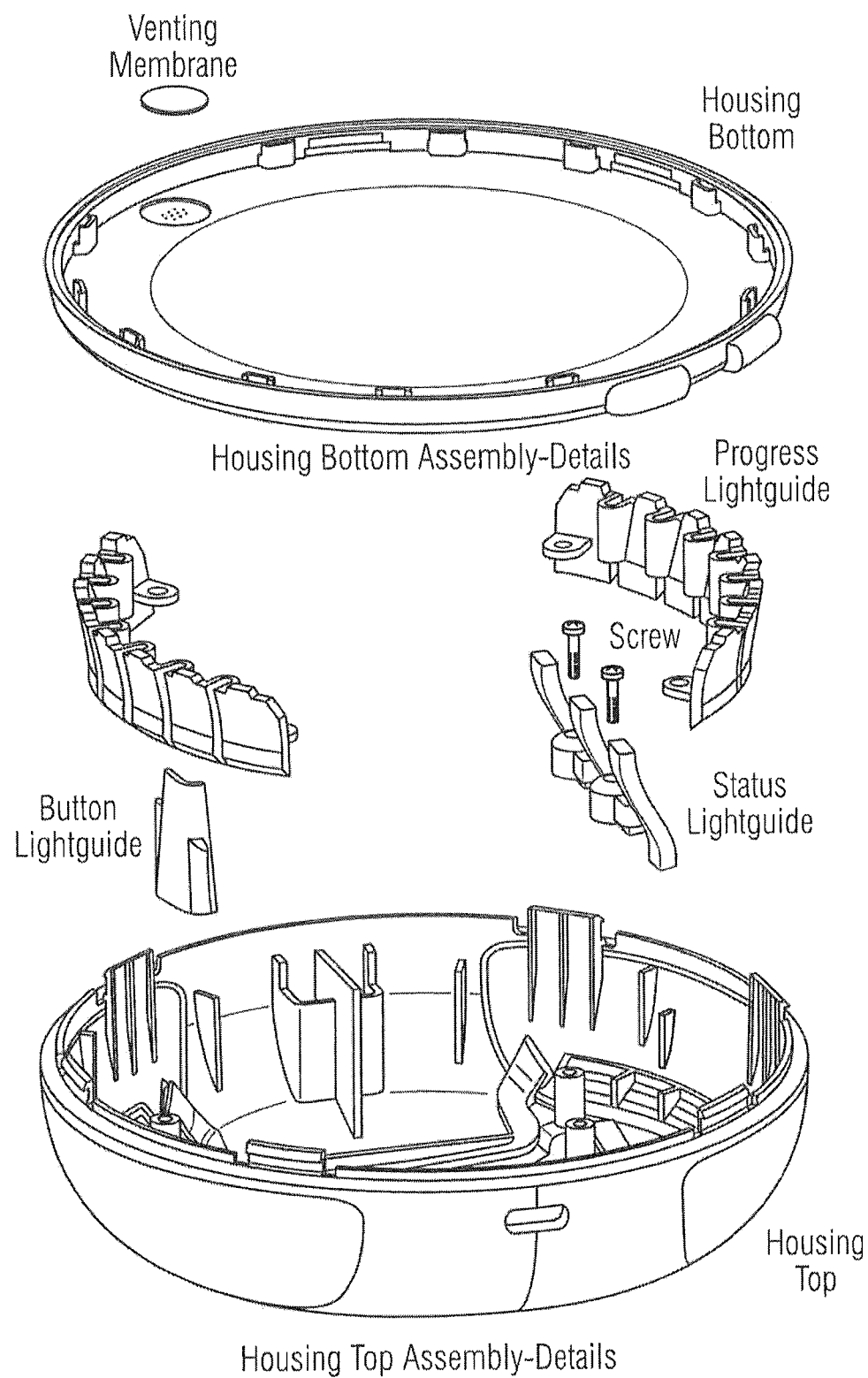
FIG. 10 shows a schematic illustration of parts of a device according to some example implementations as described herein.

FIG. 10 shows a schematic illustration of parts of the device according to some example implementations as described herein in a dismantled state.

In this example, a venting membrane is provided in the housing bottom. This may be particularly useful in case the device is attached to the body part of the patient using under-pressure. The progress light guide, button light guide and status light guide are arranged, in this example, within the housing top and fixed, in this example, via screws.

Figure 11:
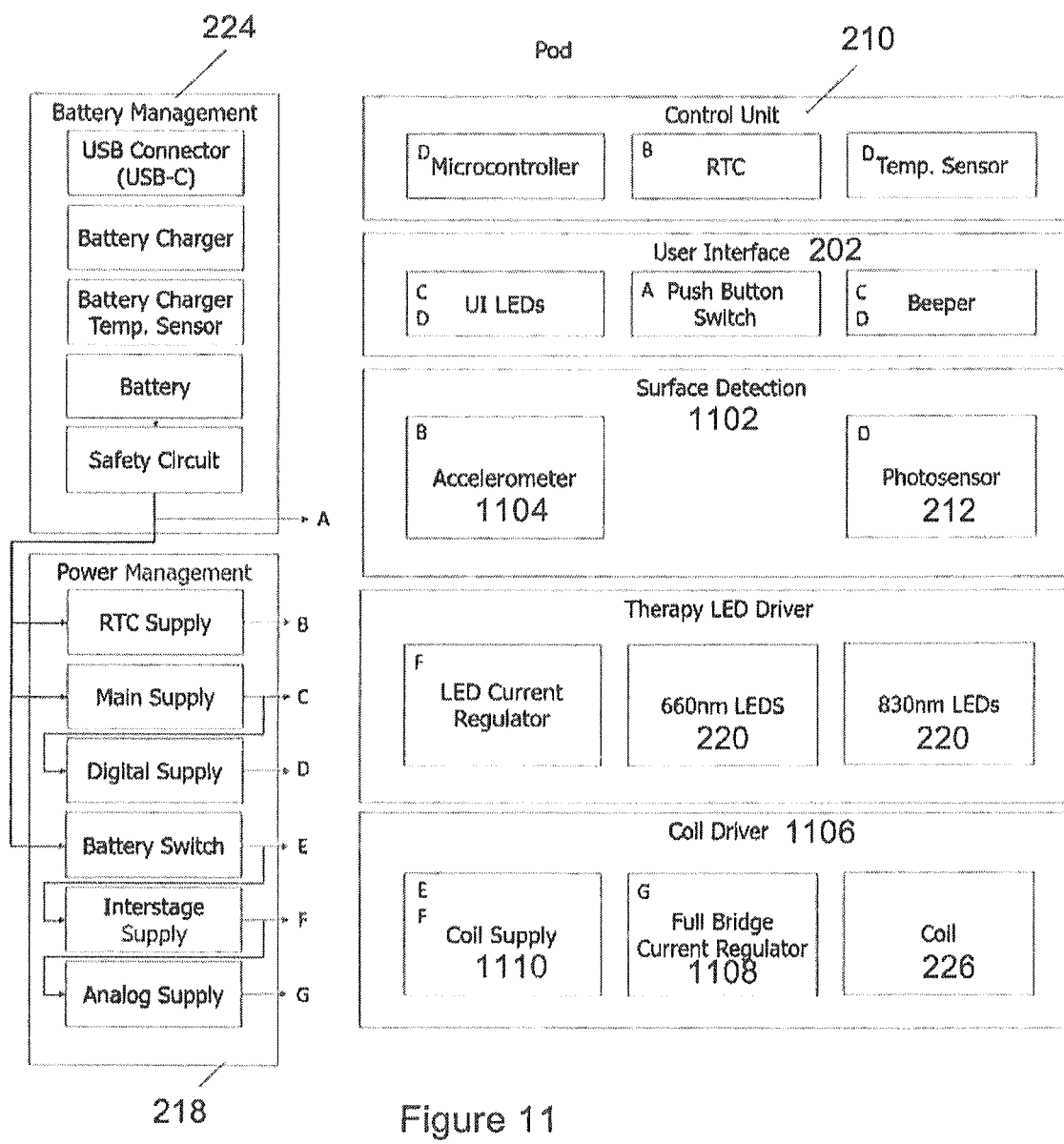
FIG. 11 shows a schematic block diagram of components of a device according to some example implementations as described herein.

FIG. 11 shows a schematic block diagram of components of a device according to some example implementations as described herein.

In this example, the device comprises a control unit 210 with a microcontroller, an RTC and a temperature sensor.

The device further comprises, in this example, a user interface 202 with user interface LEDs, a push button switch and a beeper used, for example, for audible feedback provided to the user of the device.

The device further comprises, in this example, a surface detection unit 1102 which comprises an accelerometer 1104 and a photosensor 212, as outlined above.

Furthermore, in this example, the device comprises a therapy LED driver which comprises an LED current regulator, (for example four) 660 nm LEDs 220 and (for example four) 830 nm LEDs 220.

Furthermore, in this example, the device comprises a coil driver 1106 which comprises, in this example, a coil supply 1110 (in this example with specifications of 0.8-2.5V and 7 A), a full bridge current regulator 1108 and a coil 226.

In this example, the device comprises a battery management unit 224. The battery management unit 224 comprises, in this example, a USB connector (which is, in this example a USB-C connector), a battery charger, a battery temperature sensor, a battery and a safety circuit.

Further still, in this example, the device comprises a power management unit 218, which comprises an RTC supply (in this example with specifications of 2.2V/3.3V /0.02 A), a main supply (with specifications, in this example, of 4.5V and 0.5 A), a digital supply (with specifications, in this example, of 3.3V and 0.1 A), a battery switch, an interstage supply (with specifications, in this example, of 12V and 2 A) and an analogue supply (with specifications, in this example, of 5V and 0.1 A).

The coupling of the battery management unit 224 and power management unit 218 with components of the control unit, the user interface, the surface detection unit, the therapy LED driver and the coil driver is indicated in FIG. 11 (A to G).

The Safety Circuit stands, in this example, between the Battery and the Power Management block to supervise and protect the battery. In this example, the Battery directly powers the Button, RTC Supply, Main Supply and the Battery Switch, so that they all permanently receive power from the battery unless, for example, the Safety Circuit intervenes. The RTC and the Accelerometer are both powered, in this example, by the RTC Supply and are also permanently on. Main Supply powers, in this example, the Digital Supply, the UI LEDs and the Beeper.

In this example, the Digital Supply in turn powers the Microcontroller, Temperature Sensors, driving circuits of the UI LEDs, driving circuits of the Beeper, the and the Photosensor.

The Battery Switch is used, in this example, to turn the power to the therapy hardware on (Therapy LEDs and Coil). It may directly power the Interstage Supply which may then provide power to the LED Current Regulator and the Coil Supply. (Powering the Coil Supply directly through the Battery Switch is only an assembly option.) Additionally, the Full Bridge Current Regulator is powered, in this example, by the 5V Analog Supply (and by the Coil Supply, but this is not shown in the block diagram).

Figure 12:
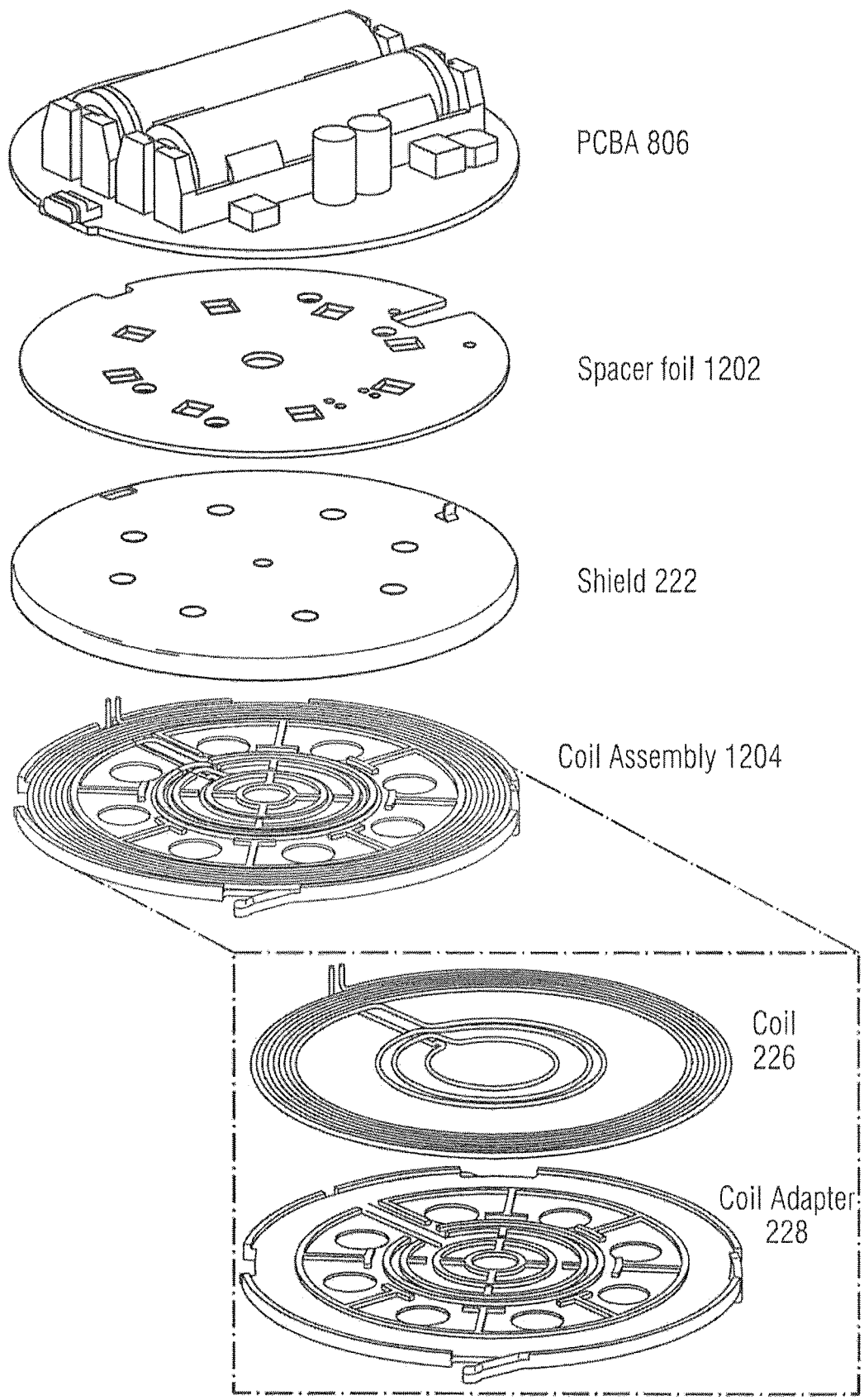
FIG. 12 shows a schematic illustration of components of a device according to some example implementations as described herein.

FIG. 12 shows a schematic illustration of components of a device according to some example implementations as described herein in a dismantled state.

In this example, the device comprises a printed circuit board assembly 806, followed by a spacer foil 1202, a magnetic field shield 222, and a coil assembly 1204 which comprises a coil 226 and a coil adapter 228. The various components are outlined in more detail below.

Figure 13A:
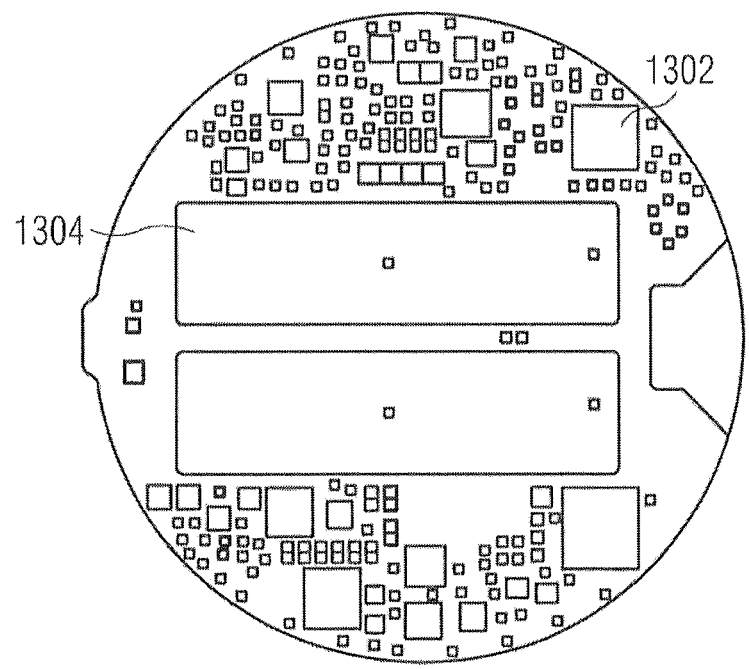
FIGS. 13a and b show schematic illustrations of a PCB top and PCB bottom, respectively, according to some example implementations as described herein.

FIGS. 13*a* and *b* show schematic illustrations of a PCB top and PCB bottom, respectively, according to some example implementations as described herein.

As shown in FIG. 13*a*, the PCB top comprises, in this example, an MCU 1302 and battery positions 1304.

Figure 13B:
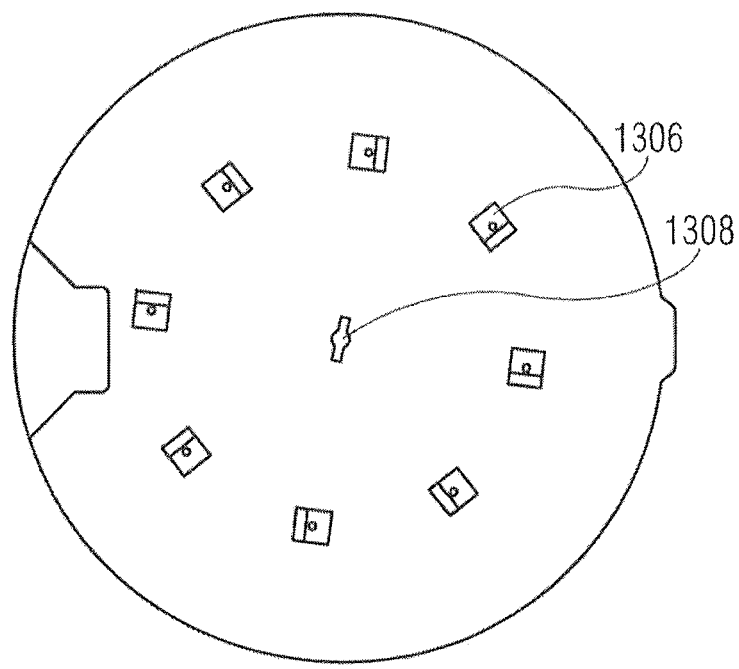

As illustrated in FIG. 13*b*, the PCB bottom comprises, in this example, eight LEDs 1306 (in this example four 660 nm and four 830 nm LEDs) and a surface detection sensor 1308 to measure if the device is placed on the body or on another surface, for example based on light reflection measurements.

The bottom layer is split, in this example, in eight segments which on the one hand spreads the heat from the LEDs, and on the other hand acts as an additional shield from magnetic fields. The magnetic field generated by the coil may induce an eddy current in the eight segments and thereby shield the ground layers behind it from the magnetic field, as outlined above.

The magnetic field from the treatment coil is attenuated, in this example, by the magnetic field shield, which may be a Mu-metal shield, by a factor of 10 to 20. The residual magnetic field induces, in this example, an eddy current in the segments on the bottom layer. These eddy currents generate a magnetic field which is inversely polarized to the treatment magnetic field and thus further reduces the impact of the treatment magnetic field on the electronics behind the segments.

Figure 14A:
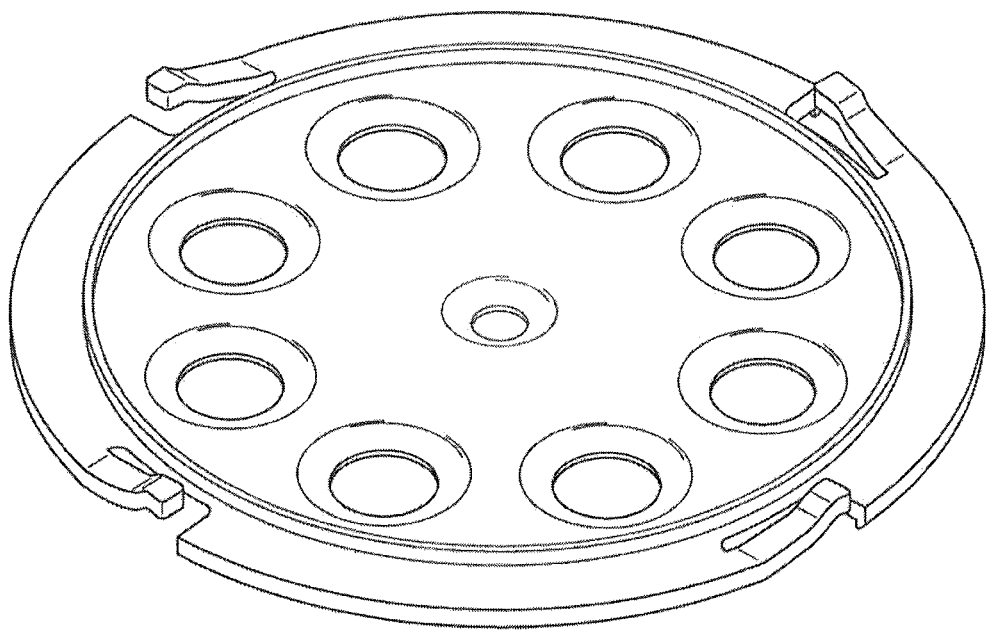
FIGS. 14a and b show schematic illustrations of a coil adapter according to some example implementations as described herein.
Figure 14B:
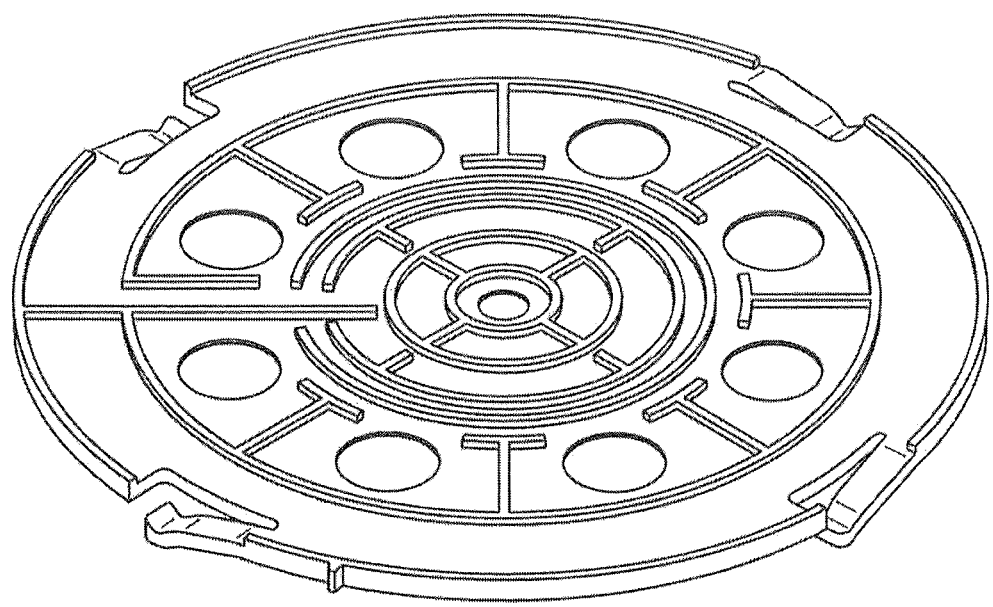

FIGS. 14*a* and *b* show schematic illustrations of a coil adapter according to some example implementations as described herein.

In some examples, the coil 226 may be glued to the coil adapter 228. The coil adapter 228 may hide the coil and the electronics (or one or more parts of the electronics) for driving the coil.

The coil adapter 228 may hold the coil (for example based on a glue interface). The coil adapter 228 may be attached to the magnetic field shield 222 (in this example via four deformable ribs).

The coil adapter 228 may provide tolerance equalization inside the device (in this example via for spring feet).

Furthermore, in this example, the coil adapter 228 comprises openings for the therapy light source (for example LEDs) and the light sensor.

Figure 15:
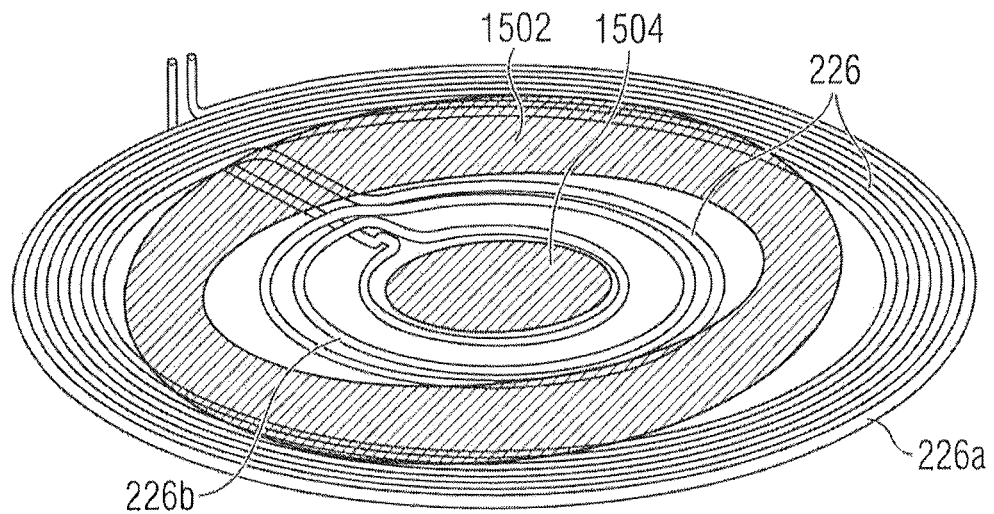
FIG. 15 shows a schematic illustration of a coil according to some example implementations as described herein.

FIG. 15 shows a schematic illustration of a coil 226 according to some example implementations as described herein.

In this example, the coil comprises openings 1502 and 1504 at locations corresponding to respective locations of the LEDs and light sensor. The wires of the coil do not lead, in this example, through these areas to avoid field disturbance in relation to the LEDs and the light sensor.

In this example, the coil 226 comprises a first set of loops 226*a* and a second set of loops 226*b*. As will be appreciated, a single loop may be provided instead of the first set of loops and/or a single loop may be provided instead of the second set of loops.

In this example, the coil is wound to have a substantially annular shape, and wherein the openings are arranged at a gap region 1502 which is provided between a first radial location of the coil comprising multiple first loops and a second radial location of the coil comprising multiple second loops.

The coil is, in this example, an insulated copper wire (PU) which is configured to generate the therapeutic magnetic field of the COMS therapy.

As outlined above, the coil bears openings 1502 and 1504 for the therapy LEDs and the light sensor (in this example at the center), respectively.

The geometry is optimized, in this example, for a homogeneous magnetic field generation within the therapy distance/area, while allowing the therapy (optical component of the COMS)/sensor light to penetrate the coil.

In some example implementations, the coil interfaces the PCB (for example by soldering).

In some examples, the coil attaches to the coil adapter (in some examples via glueing).

Figure 16:
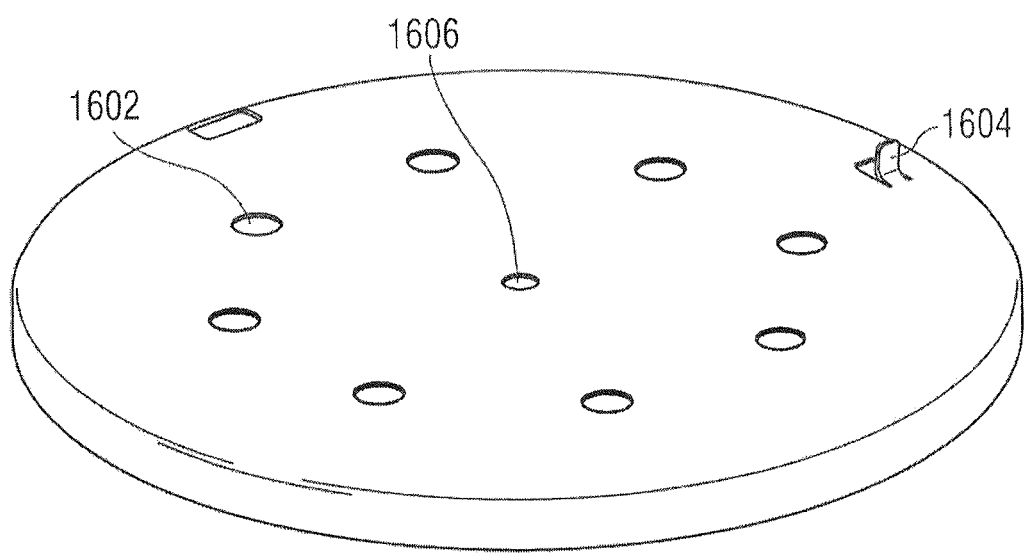
FIG. 16 shows a schematic illustration of a magnetic field shield according to some example implementations as described herein.

FIG. 16 shows a schematic illustration of a magnetic field shield 222 according to some example implementations as described herein.

In this example, the magnetic field shield comprises openings 1602 corresponding to locations of the LEDs so as to allow for the optical field of the LEDs to penetrate the magnetic field shield.

Furthermore, in this example, the magnetic field shield 222 comprises an opening 1606 arranged at the center location of the magnetic field shield 222 so as to allow for the light from the light sensor to penetrate the magnetic field shield 222.

In this example, the magnetic field shield encloses the coil and the coil adapter.

The magnetic field shield provides a high (up to or more than 50000, as outlined above) magnetic permeability material so as to efficiently shield the electronics from the magnetic field generated by the coil.

In some examples, the magnetic field shield interfaces the PCB with a flap (for example via soldering).

In this example, the magnetic field shield attaches to the coil adapter (in this example via deforming ribs).

The magnetic field shield further interfaces, in this example, the spacer foil.

In this example, the magnetic field shield further comprises an opening 1604 for the coil ends.

The thickness may be optimized for the best magnetic signal enforcement while providing a shielding between the PCB and the coil in both directions and allowing the LED/sensor light to penetrate the magnetic field shield. This may lead to reduced power consumption by being able to provide the required output.

Figure 17:
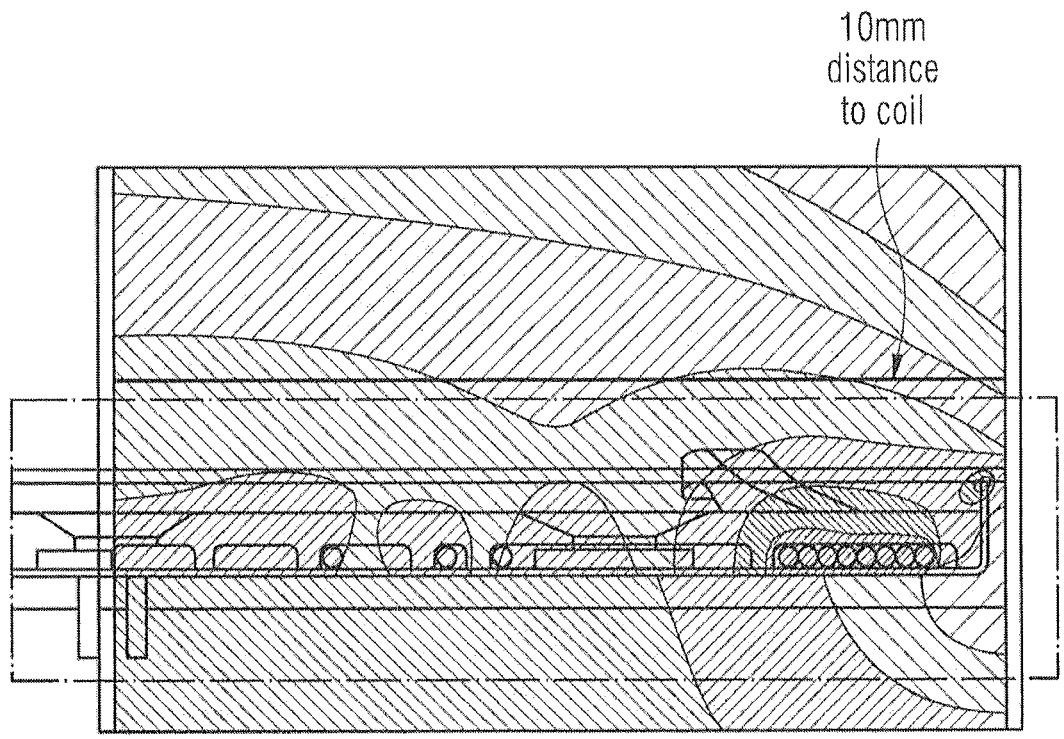
FIG. 17 shows a simulation of the magnetic field generated by the coil according to some example implementations as described herein.

FIG. 17 shows a simulation of the magnetic field generated by the coil according to some example implementations as described herein.

The magnetic field strength is, in this example, measured at a distance of 10 mm from the coil. A Mu-metal shield is provided in this example.

Measurements of the magnetic field have been shown to verify the simulation results. The same simulation model with the current coil and shield design dimensions was used for a new simulation. The magnetic field amplitudes matched the old simulation results at the points of interest (center and at r=40 mm).

Figure 18:
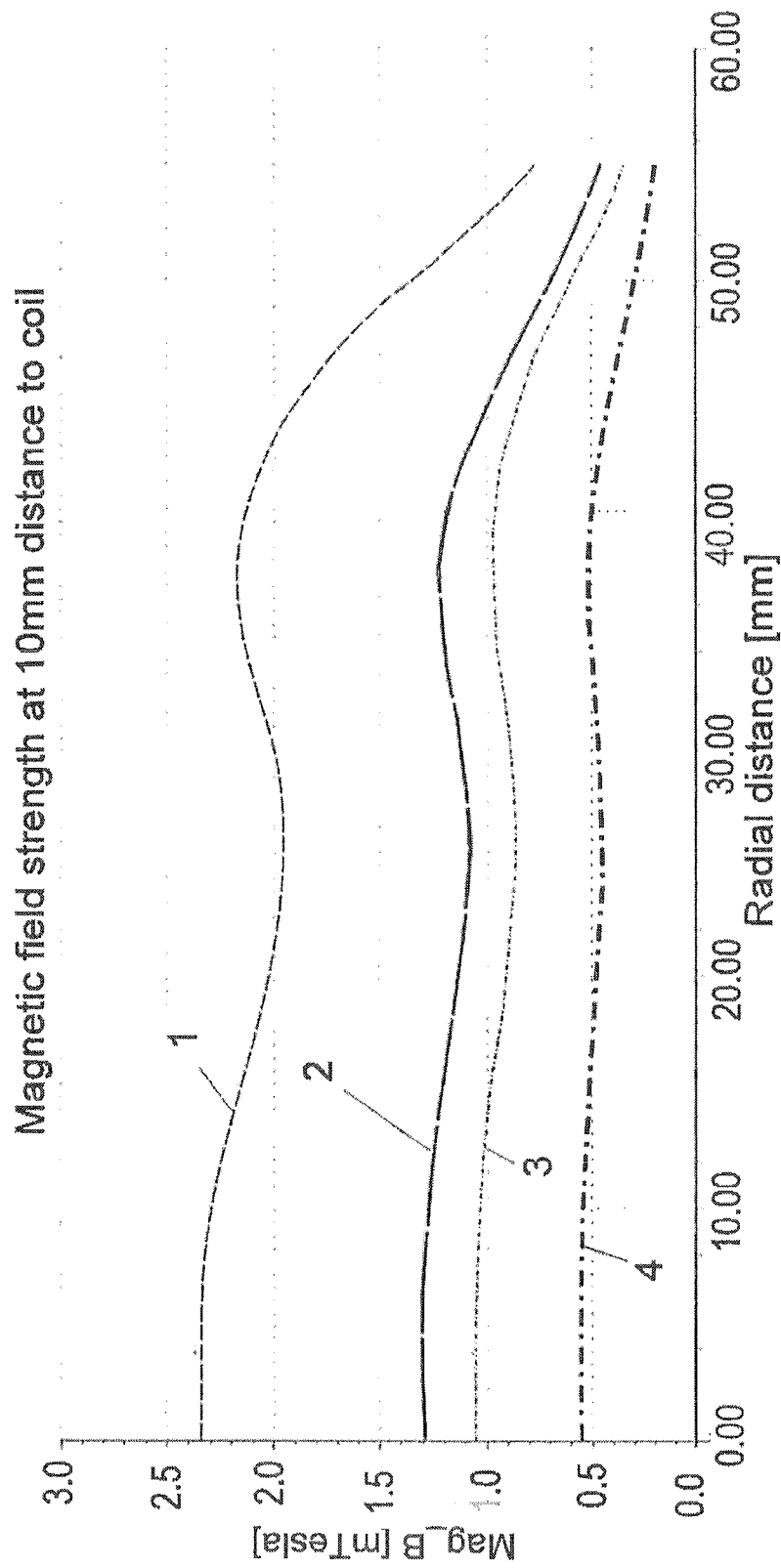
FIG. 18 shows simulations for magnetically field versus distance.

FIG. 18 shows simulations for magnetically field versus distance. The magnetic field is measured at a 10 mm distance from the coil with and without a Mu-metal sheet.

Curve 1 relates to data obtained for: Transient Time $t\_1$, Mag_B at 10 mm distance to the coil with Mu-metal shield.

Curve 2 relates to data obtained for: Transient Time $t\_1$, Mag_B at 10 mm distance to the coil without Mu-metal shield.

Curve 3 relates to data obtained for: Transient Time $t\_2$, Mag_B at 10 mm distance to the coil with Mu-metal shield.

Curve 4 relates to data obtained for: Transient Time $t\_2$, Mag_B at 10 mm distance to the coil without Mu-metal shield.

As can be seen, the strength of the magnetic field is increased by a factor of, in this example, approximately 1.7 to 2.1 when a Mu-metal sheet is used compared to the case when no magnetic field shield is implemented.

The drop in the field strength may stem, in this example, from the way the coil is designed. In some examples, there is an inner and an outer part of the coil, resulting in an inner and outer peak in the field strength. Overlaying these peaks may result in the field strength distribution. The center of the gap between the inner and outer coil lies, in this example, at 25 mm.

Comparing the curves just above 1 mT, one can see in this example that the field strength drops slightly less with the mu-metal than without the mu-metal shield. But the effect is very small and of course when comparing the curves with maximum magnitude the one with the mu-metal shield has a much larger drop than the one without the mu-metal shield.

Figure 19:
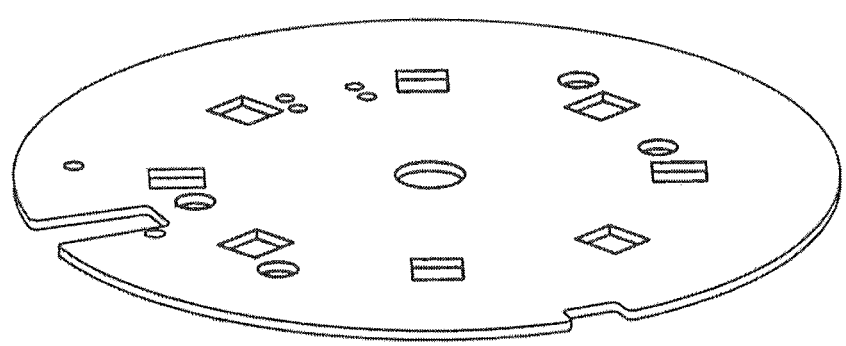
FIG. 19 shows a schematic illustration of a spacer foil according to some example implementations as described herein.

FIG. 19 shows a schematic illustration of a spacer foil according to some example implementations as described herein.

The spacer foil provides, in this example, an adhesive layer. However, it is not necessary to remove the liner as no adherence is required.

The spacer foil interfaces the PCB and the magnetic field shield. The spacer foil fills the space between the PCB and the magnetic field shield. It further bears openings for the therapeutic LEDs, the light sensor and the battery holder feet (not shown in FIG. 19). Electrical isolation which may be necessary between the PCB and the Shielding may hereby be achieved. Furthermore, mechanical fixation (for falls of device etc.) may be ensured. Further still, rattling may be prevented, whereby it may be made sure that all parts are properly fixed in position.

Figure 20:
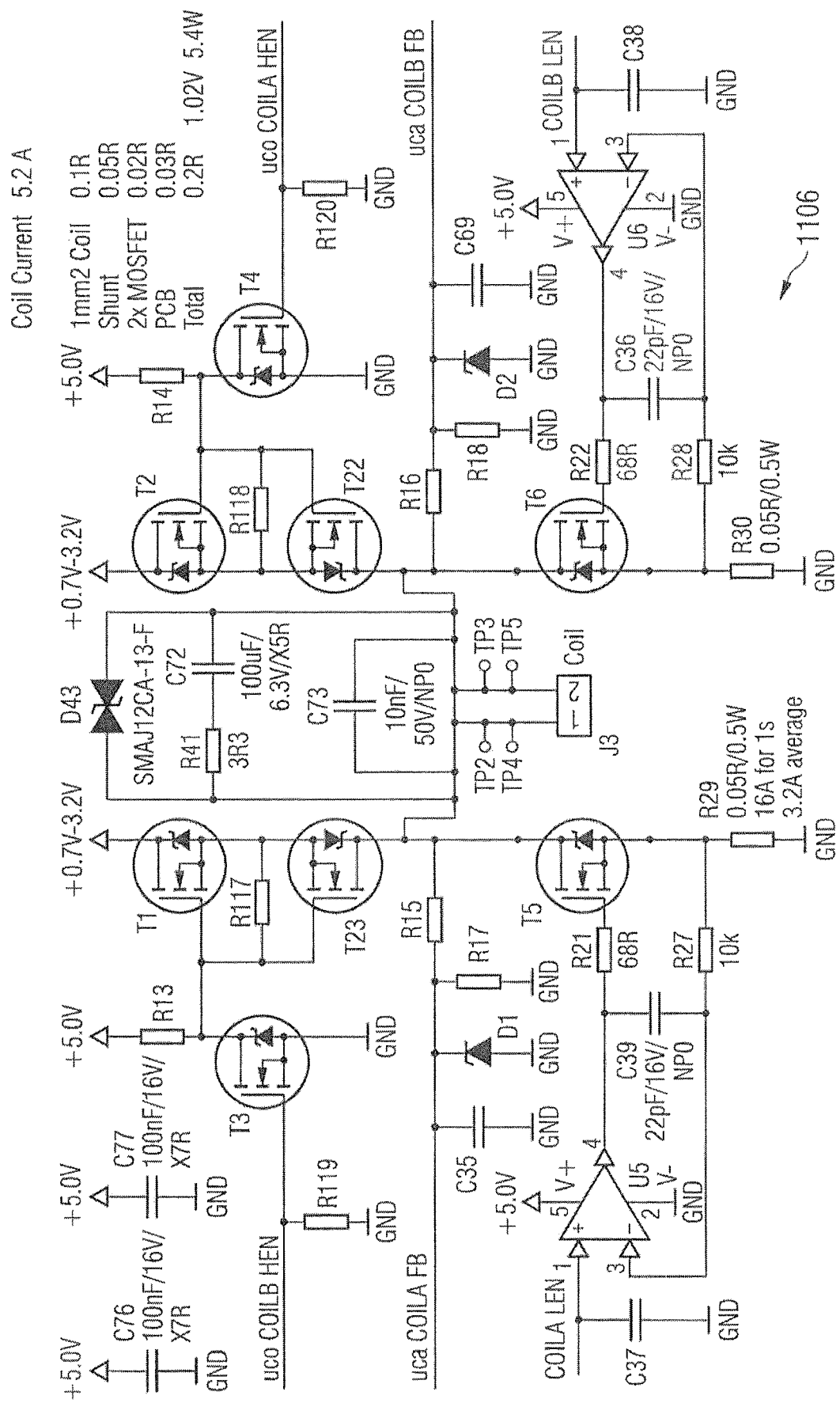
FIG. 20 shows a full bridge coil driver according to some example implementations as described herein.

FIG. 20 shows a layout of a full bridge coil driver 1106 according to some example implementations as described herein, which full bridge coil driver 1106 may be used in the device as outlined throughout the present specification.

The trapezoidal shape of the magnetic field pulse is generated, in this example, by a 1 MHz PWM signal (ucp_COILx_LEN) and a low pass filter. The four different amplitudes are generated, in this example, by activating MOSFETs T7, T8, T9 (or none of them) (not shown in the figures). Switching in hardware may increase vertical resolution of the PWM signal by a factor of four, which means, instead of 10 steps, 40 steps may be feasible. Further improvements can be reached by reducing the PWM frequency (for example to 500 kHz). This would again double the vertical resolution of the output signal. This may require slight adjustment of the low pass filter values. The output after the filter is, in this example, a trapezoid shaped signal (COILx_LEN), which is fed to the full bridge coil driver shown in FIG. 20.

U5, T5, R29 respectively U6, T6, R30 implement, in this example, a linear current regulator, controlled by the trapezoid signal COILx_LEN. The polarity of the magnetic field is selected by T1/T2 respectively uco_COILx_HEN. R27, C39 limit the bandwidth of the OPAMP to a useful level and avoid overshoot and oscillation. R21 limits the current drawn from the OPAMP and avoids overload which could reduce the performance of the OPAMP. The network R41, C72 acts as a tuned snubber to reduce overshoot in the coil current caused by the inductive load. C73 reduces EMC radiation by shorting the output for high frequency signals. The operation of the full bridge can be monitored by uca_COILx_FB and the network C35, R17, R15.

The full bridge driver comprises MOSFETs T22 and T23. These MOSFETs avoid a current flow back to the supply during the falling edge. This leads to a (usually avoided) rising voltage on T5/T6 which is required for a fast decay of the stored energy in the coil. D43 avoids destruction of the MOSFETs caused by overvoltage in case of an immediate switch-off of the low-side drivers.

The Coil Driver is located, in this example, on the top layer of the PCB, facing away from the coil with the magnetic field shield between the PCB and the coil.

The decay rate may be controlled by the low side current regulator. To ensure the coil voltage is not limited by the coil driver supply voltage, the high side may comprise two transistors (T1&T23/T2&T22) with diodes facing the opposite direction. This may allow the circuit to disconnect the coil from the coil driver supply and therefore may allow the coil voltage to become temporarily higher than the coil supply voltage (which may have been reduced to decrease power consumption) and hinder the coil current from flowing back into the coil supply.

Figure 21:
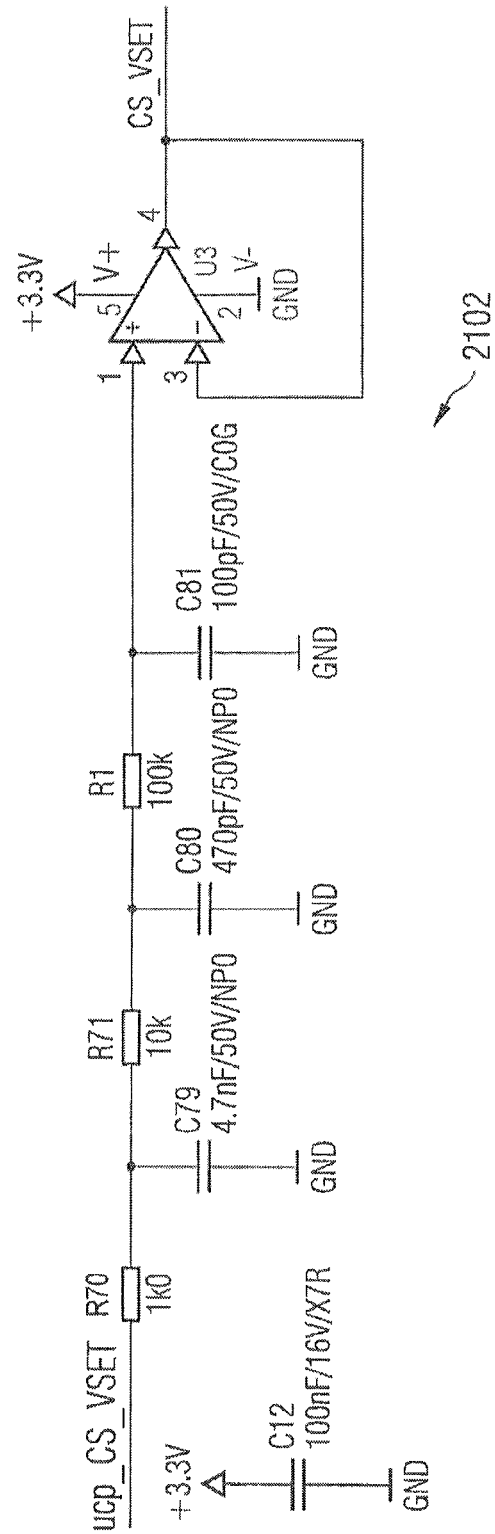
FIG. 21 shows a coil supply voltage control PWM filter according to some example implementations as described herein.

FIG. 21 shows a coil supply voltage control PWM filter 2102 according to some example implementations as described herein.

In this example, the output of the filter CS_VSET connects to the voltage feedback pin of the Coil Supply Buck Converter and allows changing the Coil Supply output voltage in the range of 0.7V . . . 3.2V.

A low pass filtered PWM signal is fed into the feedback network (R6, R7, R8) of the buck converter by R7 and allows adjusting the output voltage of the coil supply from 0.7V to 3.2V. This feature offers the opportunity to increase the supply voltage, which is necessary to reach the high di/dt of the inductive coil during the fast-rising slopes of the trapezoid signal. After the slope, the voltage can be reduced to increase the efficiency of the coil driver.

In this example, the Coil Supply Voltage Control PWM Filter controls the supply voltage of the Full Bridge Coil Driver. Faster current change rates may require higher voltages applied to the coil $$\left(\frac{di}{dt} = \frac{U}{L}\right).$$

After the current through the coil has been changed, only part of the initially required voltage may be needed to keep the current flowing ($U_L=I_L*R_L$). Since the current may be maintained by a linear current regulator, a lot of power may be dissipated there instead of the coil, draining the battery faster. To solve this, the Full Bridge Coil Driver's supply voltage can, in this example, be adjusted to meet both the high current change rates and an efficient use of the battery power.

Figure 22:
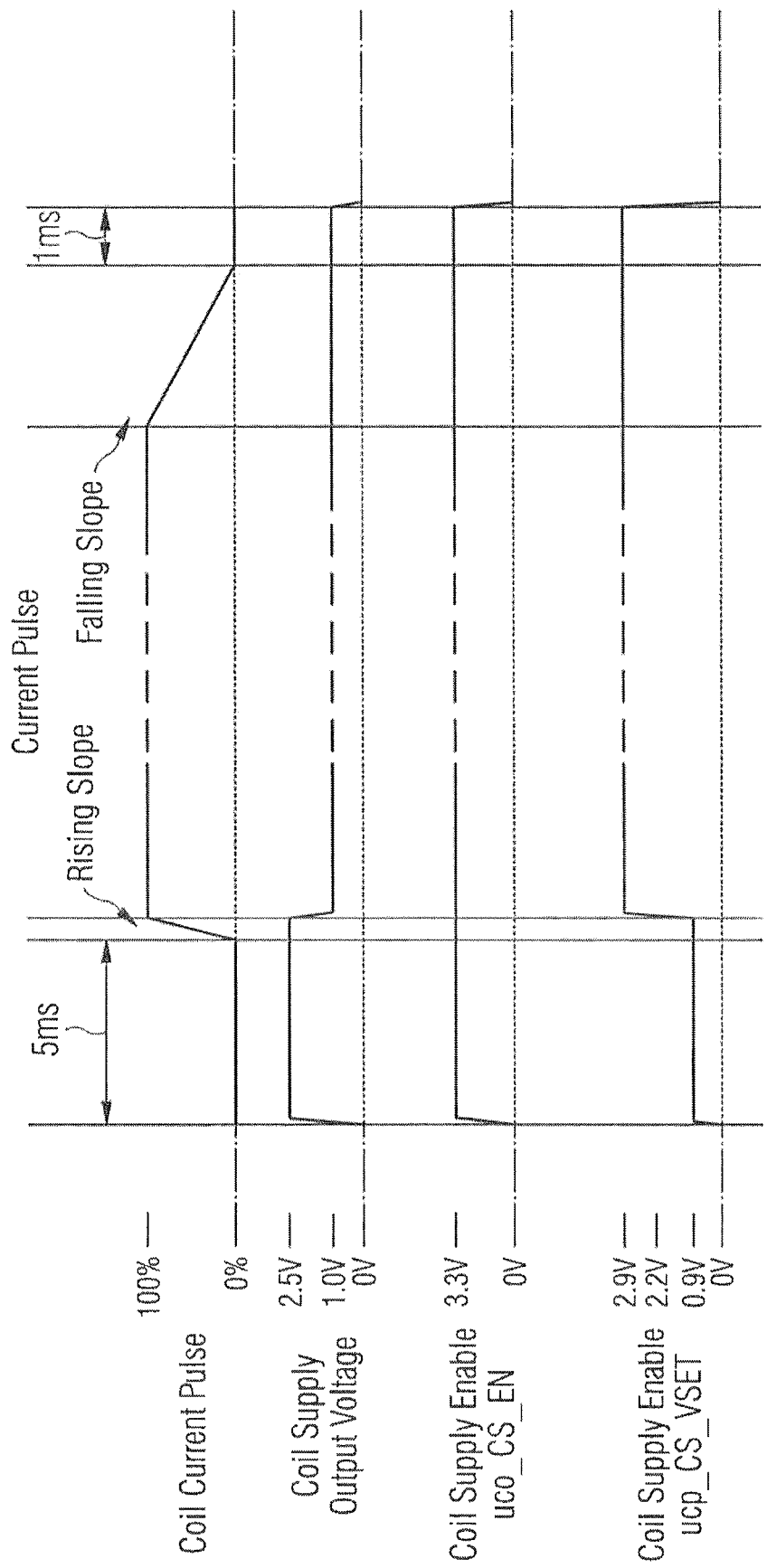
FIG. 22 shows a graph of a coil control signal timing according to some example implementations as described herein.

FIG. 22 shows a graph of a coil control signal timing according to some example implementations as described herein. Using the elements depicted in FIGS. 20 and 21, as can be seen in FIG. 22, a fast increase and decrease of the pulse with very good efficiency can be provided.

As outlined above, the device may comprise a photo/light sensor. The device may target a surface (usually the skin of the patient) if it is attached/mounted properly. The surface may reflect the light emitted by the illumination LEDs. The reflected light may be measured by the light sensor which is placed, in some examples, towards the patient in the center of the device. The sensor is configured to detect a surface and the light may only be activated if a surface is present.

The amount of light reflected may be highly variable given the operating and surrounding circumstances and conditions and may depend on the distance to the surface, the structure, the color and the reflection/scattering parameter of the surface.

The light sensor may provide, in some examples, for five different channels (red, green, blue, white and infrared) and may provide an opportunity of foreign light compensation. In some examples, the light sensor is a digital sensor with an I2C interface.

Furthermore, as outlined above, the device may further comprise an accelerometer. The accelerometer may be configured to detect when the device is placed on a flat surface like a table. In this case, activation of the device may be prevented.

The device may further comprise a coil current regulation which regulates the coil current in the COMS therapy. The voltage may be regulated on the coil.

When combining magnetic stimulation and photo animation technology, the PCB with LEDs may need to be close to the coil, in which case, however, the magnetic field may induce eddy currents on the PCB which may disturb the complete electronic.

The device as described herein combines magnetic stimulation (for example (quasi-)trapezoidal pulses with 20 Hz and 0.4-1.6 mT, for example in three steps) and photon emission therapy (in some examples, at wavelengths of 660 and 830 nm).

A thin (for example between 0.1 and 5 mm) sheet (i.e. shield) may be arranged between the PCB and the coil.

Preferably, a Mu-metal (for example nickel-iron soft ferromagnetic alloy) or any other material with a very high permeability may be used for the magnetic field shield.

Holes (for example 8 LEDs plus 1 light sensor) may be provided in the magnetic field shield to allow the LEDs from the PCB to shine through the magnetic field shield.

The coil may, in some examples, comprise 1 to 100 windings (for example 5 to 15 windings) and may be made of a wire having a thickness of 1.2 mm.

The device may be powered by a small battery and DC-DC converters to achieve the high currents necessary.

The magnetic field shield may comprise sidewalls to prevent that the field goes around the corner of the magnetic field shield.

The configuration of the device as described herein allows for the LEDs (or generally the light source) to be arranged relatively close to the coil. This allows for a compact and portable design of the device. In particular, it has thus far been a challenge to apply to different technologies to such a small surface/device. A compact design of the device (lightweight) further helps ensuring easy application and efficiency of therapy.

The device as described according to the example implementations as described herein allows for very consistent magnetic fields. A very homogeneous magnetic field distribution can be achieved. It may be important to homogenize the therapeutic application for different indications/locations.

The device according to the example implementations as described herein further allows for an energy efficient design. At the same time, the magnetic field shielding makes the device more efficient. The device is less heavy and less heating of the device can be ensured.

Via the shielding, no or very little eddy currents may be generated on the PCB. The device may be configured to allow generation of eddy currents which may be polarized oppositely to the therapeutic magnetic field so as to minimize any effects of the magnetic field on the electric circuit.

FIGS. 23a to d show schematic illustrations of a consumable according to some example implementations as described herein. As can be seen, the consumable has, in this example, a substantially annular shape and may be made of a material which is translucent for the optical field stemming from the light source (for example LEDs). The flexible consumable may conform to the body part of the patient to which the device is to be applied, as can be seen in FIG. 23d.

When combining magnetic stimulation and photon emission technology to treat a wound of the patient, the device may need to be close to the wound but at the same time it should not hurt the wound sides and prevent cross contamination.

The consumable may be used for a sterile single use to allow soft interface of the device to the wound.

A strap may be used in order to fix the device via the consumable to the patient.

A mechanism is, in some examples, provided to allow easy fixation of the device to the soft part.

The consumable may, in some examples, comprise two parts moulded together. This may allow easy fixation while ensuring soft adaptation to the patient.

An audible feedback may be provided so as to indicate to the user when the consumable is clicked to the non-consumable part of the device.

In some examples, the harder part of the consumable may be formed in a ring-shape. Additionally or alternatively, the hard part may be translucent and/or biocompatible and/or be made of a ring instead of a circle.

The consumable may allow for soft fixation of the device in a close, defined distance to the wound, which further allows for precise control of exposure of the wound to the optical and magnetic fields.

The consumable may be deformable. Some parts of the consumable may be made of silicon. A spring mechanism and 3D fitting mechanism of the silicon may allow for optimal and comfortable attachment to the body parts of the patient to be treated. This may result in decreased pressure points/edema, while ensuring easy application, and increasing efficiency of the therapy by applying the device in a defined distance.

A user friendly indication is provided in some examples via a click-in which gives feedback for correct placement, and allows fixation directly from the sterile packaging trays so that the consumable is not touched by the healthcare professional or the patient.

The consumable protects the device from wound exudates. It therefore provides for a biocompatible, soft layer that protects the device from exudates but allows therapy light to pass through it and also enables light reflection measurements.

The consumable prevents cross-contamination for sterility. In some examples, the consumable may be used for a single use and the consumable as a sterile component prevents all types of cross-contamination.

The sensor measurements and therapy application may be performed on a highly transparent area above the treatment area of the patient.

The following clauses are also encompassed by the present disclosure and may fully or partly be incorporated into other example implementations and embodiments as described herein.

1. An optical and magnetic stimulation, OMS, wound therapy device comprising:
   a light source configured to generate an optical field for an OMS wound therapy;
   an electric circuit coupled to the light source for driving the light source to generate the optical field;
   a coil configured to generate a magnetic field for the OMS wound therapy; and
   a magnetic field shield arranged between the coil on the one hand and the light source and electric circuit on the other hand, and wherein the magnetic field shield is configured to shield the electric circuit and the light source from the magnetic field generated by the coil.

2. An OMS wound therapy device as specified in clause 1, wherein the OMS wound therapy device is configured to generate, using the coil and the magnetic field shield, an attenuated magnetic field, on a side of the magnetic field shield on which the electric circuit and light source are arranged, to induce, based on the attenuated magnetic field, an eddy current in a layer of the OMS wound therapy device in or on which the electric circuit is arranged.

3. An OMS wound therapy device as specified in clause 1 or 2, wherein the magnetic field shield comprises a material having a relative magnetic permeability of more than 5000, preferably more than 10000, more preferably more than 20000, and more preferably more than 50000.

4. An OMS wound therapy device as specified in any preceding clause, wherein the magnetic field shield comprises one or more magnetic field shield openings through which the optical field can penetrate for irradiating a wound of a patient.

5. An OMS wound therapy device as specified in any preceding clause, wherein the magnetic field shield comprises one or more side walls configured to prevent the magnetic field from penetrating through to the electric circuit and the light source via an edge or corner region of the magnetic field shield.

6. An OMS wound therapy device, in particular as specified in any preceding clause, wherein the OMS wound therapy device comprises a coil voltage supply coupled to a bridge coil driver for driving the coil to generate a pulsed modulated magnetic field.

7. An OMS wound therapy device as specified in clause 6, wherein the bridge coil driver comprises a first transistor configured to prevent a current from flowing back to the coil voltage supply during a falling edge of a pulse of the pulsed modulated magnetic field.

8. An OMS wound therapy device as specified in clause 7, wherein the bridge coil driver comprises a linear current regulator comprising a second transistor, wherein the second transistor is coupled with the first transistor, and wherein the bridge coil driver is configured, based on the current being prevented, via the first transistor, from flowing back to the coil voltage supply during the falling edge of the pulse, to induce a rising voltage on the second transistor during the falling edge of the pulse.

9. An OMS wound therapy device as specified in clause 7 or 8, wherein the bridge coil driver further comprises a Zener diode coupled with the first and second transistors, and wherein the Zener diode is configured to prevent the first and second transistors to be damaged due to an overvoltage during a switch-off of the bridge coil driver.

10. An OMS wound therapy device as specified in any one of clauses 6 to 9, further comprising a coil supply voltage control filter and a buck converter coupled to the coil voltage supply for adjusting an output voltage of the coil voltage supply.

11. An OMS wound therapy device as specified in any preceding clause, wherein the light source comprises a plurality of LEDs, and wherein a layer of the OMS wound therapy device on which the LEDs are arranged is split into a plurality of segments, wherein each of the segments comprises one or more of the plurality of LEDs.

12. An OMS wound therapy device as specified in clause 11, wherein the coil is wound to comprise openings at locations corresponding to respective locations of the LEDs to allow penetration of the optical field through the coil.

13. An OMS wound therapy device as specified in clause 12, wherein the coil is wound to have a substantially annular shape, and wherein the openings are arranged at a gap region which is provided between a first radial location of the coil comprising a first loop and a second radial location of the coil comprising a second loop.

14. An OMS wound therapy device as specified in any preceding clause, further comprising a distance sensor configured to determine whether a surface is within a predefined distance to the OMS wound therapy device, and wherein the OMS wound therapy device is configured to generate one or both of the optical field and the magnetic field only if the surface is within the predefined distance to the OMS wound therapy device.

15. An OMS wound therapy device as specified in any preceding clause, further comprising an optical sensor configured to detect one or more of:
an amount of light reflected from a surface;
a color of the surface, wherein the OMS wound therapy device is configured to correlate the color of the surface with a color code for a wound stored in a memory of the OMS wound therapy device;
a surface structure of the surface, wherein the OMS wound therapy device is configured to correlate the surface structure with a surface structure stored in the memory of the OMS wound therapy device; and
a reflection and/or scattering parameter of the surface; and
wherein the OMS wound therapy device is configured to determine, based on one or more of the amount of light reflected from the surface, the color of the surface, the surface structure of the surface and the reflection and/or scattering parameter of the surface, whether the surface belongs to a wound, and wherein the OMS wound therapy device is configured to generate one or both of the optical field and the magnetic field only if the surface is determined to belong to a said wound.

16. An OMS wound therapy device as specified in any preceding clause, further comprising an accelerometer, and wherein the OMS wound therapy device is configured to:
determine, via the accelerometer, whether the OMS wound therapy device is placed on an unlively object, and
if the OMS wound therapy device is determined to be placed on a said unlively object, prevent the optical field and/or the magnetic field from generatable.

17. An OMS wound therapy device, in particular as specified in any preceding clause, comprising a flexible consumable for attaching the OMS wound therapy device to a wound of a patient, and wherein a distance between a said wound and the light source and the coil, respectively, is adjustable by varying a depression state of the flexible consumable.

18. An OMS wound therapy device, in particular as specified in clause 17, wherein the flexible consumable is configured to conform to a shape of a body part of the patient to which the OMS wound therapy device is to be attached.

19. An OMS wound therapy device as specified in clause 17 or 18, wherein the OMS wound therapy device comprises a non-consumable part which comprises the light source, the electric circuit, the coil and the magnetic field shield, and wherein the OMS wound therapy device is configured to provide an audible feedback when the consumable is attached to the non-consumable part.

20. An OMS wound therapy device as specified in any one of clauses 17 to 19, wherein the flexible consumable has a substantially ring shape and/or wherein the flexible consumable is translucent to the optical field.

21. An OMS wound therapy device as specified in any one of clauses 17 to 20, wherein the flexible consumable is configured to be attachable to a said wound based on a pressure-reduced attachment mechanism.

22. An OMS wound therapy device as specified in any preceding clause, wherein the light source is configured to emit light having a (first) wavelength of approximately 660 nm and/or a (second) wavelength of approximately 830 nm.

23. An OMS wound therapy device as specified in any preceding clause, wherein the light source is configured to emit light having a (third) wavelength between approximately 400 nm and 430 nm.

24. A method of treating a wound of a patient using the OMS wound therapy device as specified in any preceding clause.

25. A method as specified in clause 24, further comprising triggering an electronic phase transition in mitochondrial cytochrome C oxidase in the wound by irradiating the wound with light of a wavelength of approximately 660 nm and/or approximately 830 nm.

26. A method as specified in clause 24 or 25, further comprising inducing an increase in reactive oxygen species in the wound by irradiating the wound with light of a wavelength of approximately 400 nm to 430 nm.

27. Use of the OMS wound therapy device as specified in any one of clauses 1 to 23 for wound therapy treatment, in particular using light of a wavelength of approximately 660 nm and/or approximately 830 nm and/or approximately 400 nm to 430 nm.

No doubt many other effective alternatives will occur to the skilled person. It will be understood that the invention is not limited to the described embodiments and encompasses modifications apparent to those skilled in the art and lying within the scope of the claims appended hereto.

The invention claimed is:

1. An optical and magnetic stimulation, OMS, wound therapy device comprising:
   a light source configured to generate an optical field for an OMS wound therapy;
   an electric circuit coupled to the light source for driving the light source to generate the optical field;
   a coil configured to generate a magnetic field for the OMS wound therapy; and
   a magnetic field shield comprising a sheet, wherein the coil is arranged on a first side of the sheet, and the light source and electric circuit are arranged on a second side of the sheet, wherein the first side is opposite to the second side, and wherein the magnetic field shield is configured to shield, by attenuating, on the second side of the sheet, the magnetic field generated by the coil by a factor of ten to twenty, the electric circuit and the light source from the magnetic field generated by the coil.

2. The OMS wound therapy device as claimed in claim 1, wherein the OMS wound therapy device is configured to generate, using the coil and the magnetic field shield, an attenuated magnetic field, on the second side of the sheet, to induce, based on the attenuated magnetic field, an eddy current in a layer of the OMS wound therapy device in or on which the electric circuit is arranged.

3. The OMS wound therapy device as claimed in claim 1, wherein the magnetic field shield comprises a material having a relative magnetic permeability of more than 5000.

4. The OMS wound therapy device as claimed in claim 1, wherein the magnetic field shield comprises one or more magnetic field shield openings through which the optical field can penetrate for irradiating a wound of a patient.

5. The OMS wound therapy device as claimed in claim 1, wherein the magnetic field shield comprises one or more side walls configured to prevent the magnetic field from penetrating through to the electric circuit and the light source via an edge or corner region of the magnetic field shield.

6. The OMS wound therapy device as claimed in claim 1, wherein the OMS wound therapy device comprises a coil voltage supply coupled to a bridge coil driver for driving the coil to generate a pulsed modulated magnetic field.

7. The OMS wound therapy device as claimed in claim 6, wherein the bridge coil driver comprises a first transistor configured to prevent a current from flowing back to the coil voltage supply during a falling edge of a pulse of the pulsed modulated magnetic field.

8. The OMS wound therapy device as claimed in claim 7, wherein the bridge coil driver comprises a linear current regulator comprising a second transistor, wherein the second transistor is coupled with the first transistor, and wherein the bridge coil driver is configured, based on the current being prevented, via the first transistor, from flowing back to the coil voltage supply during the falling edge of the pulse, to induce a rising voltage on the second transistor during the falling edge of the pulse;
and/or
wherein the bridge coil driver further comprises a Zener diode coupled with the first and second transistors, and wherein the Zener diode is configured to prevent the first and second transistors to be damaged due to an overvoltage during a switch-off of the bridge coil driver.

9. The OMS wound therapy device as claimed in claim 6, further comprising a coil supply voltage control filter and a buck converter coupled to the coil voltage supply for adjusting an output voltage of the coil voltage supply.

10. The OMS wound therapy device as claimed in claim 1, wherein the light source comprises a plurality of LEDs, and wherein a layer of the OMS wound therapy device on which the LEDs are arranged is split into a plurality of segments, wherein each of the segments comprises one or more of the plurality of LEDs.

11. The OMS wound therapy device as claimed in claim 10, wherein the coil is wound to comprise openings at locations corresponding to respective locations of the LEDs to allow penetration of the optical field through the coil.

12. The OMS wound therapy device as claimed in claim 11, wherein the coil is wound to have an annular shape, and wherein the openings are arranged at a gap region which is provided between a first radial location of the coil comprising a first loop and a second radial location of the coil comprising a second loop.

13. The OMS wound therapy device as claimed in claim 1, further comprising a distance sensor configured to determine whether a surface is within a predefined distance to the OMS wound therapy device, and wherein the OMS wound therapy device is configured to generate one or both of the optical field and the magnetic field only if the surface is within the predefined distance to the OMS wound therapy device.

14. The OMS wound therapy device as claimed in claim 1, further comprising an optical sensor configured to detect one or more of:
   an amount of light reflected from a surface;
   a color of the surface, wherein the OMS wound therapy device is configured to correlate the color of the surface with a color code for a wound stored in a memory of the OMS wound therapy device;
   a surface structure of the surface, wherein the OMS wound therapy device is configured to correlate the surface structure with a surface structure stored in the memory of the OMS wound therapy device; and
   a reflection and/or scattering parameter of the surface; and
   wherein the OMS wound therapy device is configured to determine, based on one or more of the amount of light reflected from the surface, the color of the surface, the surface structure of the surface and the reflection and/or scattering parameter of the surface, whether the surface belongs to the wound, and wherein the OMS wound therapy device is configured to generate one or both of the optical field and the magnetic field only if the surface is determined to belong to said wound.

15. The OMS wound therapy device as claimed in claim 1, further comprising an accelerometer, and wherein the OMS wound therapy device is configured to:
   determine, via the accelerometer, whether the OMS wound therapy device is placed on an inanimate object, and
   if the OMS wound therapy device is determined to be placed on said inanimate object, prevent the optical field and/or the magnetic field from being generatable.

16. The OMS wound therapy device as claimed in claim 1, further comprising a flexible consumable for attaching the OMS wound therapy device to a wound of a patient, and wherein a distance between said wound and the light source and the coil, respectively, is adjustable by varying a depression state of the flexible consumable.

17. The OMS wound therapy device as claimed in claim 16, wherein the flexible consumable is configured to conform to a shape of a body part of the patient to which the OMS wound therapy device is configured to be attached.

18. The OMS wound therapy device as claimed in claim 16, wherein the OMS wound therapy device comprises a non-consumable part which comprises the light source, the electric circuit, the coil and the magnetic field shield, and wherein the OMS wound therapy device is configured to provide an audible feedback when the flexible consumable is attached to the non-consumable part.

19. The OMS wound therapy device as claimed in claim 16, wherein the flexible consumable has a ring shape and/or wherein the flexible consumable is translucent to the optical field; and/or wherein the flexible consumable comprises a pressure-reduced attachment mechanism via which the flexible consumable is configured to be attachable to said wound.

20. The OMS wound therapy device as claimed in claim 1, wherein the light source is configured to emit light having a first wavelength of approximately 660 nm and/or a second wavelength of approximately 830 nm; and/or wherein the light source is configured to emit light having a third wavelength between approximately 400 nm and 430 nm.

21. A method of treating a wound of a patient using an optical and magnetic stimulation (OMS) wound therapy device, the OMS wound therapy device comprising:

a light source configured to generate an optical field for an OMS wound therapy;
   an electric circuit coupled to the light source for driving the light source to generate the optical field;
   a coil configured to generate a magnetic field for the OMS wound therapy; and
   a magnetic field shield comprising a sheet, wherein the coil is arranged on a first side of the sheet and the light source and electric circuit are arranged on a second side of the sheet, wherein the first side is opposite to the second side, and wherein the magnetic field shield is configured to shield, by attenuating, on the second side of the sheet, the magnetic field of the coil by a factor of ten to twenty, the electric circuit and the light source from the magnetic field generated by the coil;
   wherein the method comprises:
   driving the light source to generate the optical field, and driving the coil to generate the magnetic field.

* * * * *